US008019557B2

(12) United States Patent
Murali et al.

(10) Patent No.: US 8,019,557 B2
(45) Date of Patent: *Sep. 13, 2011

(54) CAVITY INDUCED ALLOSTERIC MODIFICATION OF INTERMOLECULAR INTERACTIONS AND METHODS OF IDENTIFYING COMPOUNDS THAT EFFECT THE SAME

(75) Inventors: Ramachandran Murali, Swarthmore, PA (US); Mark I. Greene, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/632,221

(22) Filed: Dec. 7, 2009

(65) Prior Publication Data

US 2010/0151507 A1 Jun. 17, 2010

Related U.S. Application Data

(63) Continuation of application No. 09/720,647, filed as application No. PCT/US99/15062 on Jul. 1, 1999, now Pat. No. 7,653,495.

(60) Provisional application No. 60/091,431, filed on Jul. 1, 1998, provisional application No. 60/133,435, filed on May 11, 1999.

(51) Int. Cl.
*G01N 31/00* (2006.01)
*G01N 33/566* (2006.01)
*A61K 38/00* (2006.01)
*C07K 1/00* (2006.01)

(52) U.S. Cl. ............ 702/27; 702/19; 436/501; 530/300; 530/350

(58) Field of Classification Search ........................ None
See application file for complete search history.

(56) References Cited

U.S. PATENT DOCUMENTS

| 5,571,825 A | 11/1996 | Boschelli et al. |
| 5,597,719 A | 1/1997 | Freed et al. |
| 7,653,495 B1 | 1/2010 | Murali et al. |

FOREIGN PATENT DOCUMENTS

| EP | 0818744 | 1/1998 |
| WO | WO 97/34589 | 9/1997 |
| WO | WO 98/49897 | 11/1998 |
| WO | WO 00/01349 | 1/2000 |

OTHER PUBLICATIONS

Aghajari et al., "Crystal structures of the psychrophilic alpha-amylase from *Alteromonas haloplanctis* in its native form and complexed with an inhibitor", Protein Science, Mar. 1998, 7(3), 564-572.

Banner et al., "Crystal Structure of the soluble human 55kd TNF receptor-human TNFβ complex: Implications for TNF receptor activation", Cell, May 7, 1993, 73(3), 431-445.

Berthold et al., "Modes of peptide binding in G proetin-coupled receptors", Neurochemical Research., Aug. 1997, 22(8),1023-1031.

Böhm, H. J., "Computational tools for structure-based ligand design", Progress in Biophysics and Molecular Biology, 1996, 66(3), 197-210.

Böhm, H.J., "A novel computational tool for automated structure-based drug design", Journal of Molecular Recognition., Sep. 1993, 6(3), 131-137.

Boteju et al., "The use of topographical constraints in receptor mapping: Investigation of topographical requirements of the tryptophan 30 residue for receptor binding of Asp-Tyr-D-Phe-Gly-Trp-(N-Me) Nle-Asp-Phe-NH2 (SNF 9007), a cholecystokinin (26-33) analogue that binds to both CCK-B and -opiod receptors", J. Med. Chem., Sep. 27, 1996, 39(20), 4120-4124.

Cho et al., "Macromolecular versus small-molecule therapeutics: drug discovery, development and clinical considerations", Trends in Biotechnology, May 1996, 14(5), 153-158.

Coffin et al., "Retroviruses at the National Center for Biotechnology Information", Cold Spring Harbor Laboratory Press, 1997, pp. 1-2.

Connolly et al., "The molecular surface package", J. Mol. Graphics, Jun. 1993, 11(2), 139-141.

D'Aquino et al., "The magnitude of the backbone conformational entrophy change in protein folding", Proteins, Jun. 1996, 25(2), 143-156.

DesJarlais et al., "docking flexible ligands to macromolecular receptors by molecular shape", J. Med. Chem, Nov. 1986, 29(11), 2149-2153.

DesJarlais et al., "Using shape complementarity as an initial screen in designing ligands for a receptor binding site of known three-dimensional structure", J. Med. Chem, Apr. 1988, 31(4), 722-729.

Dock, Version 4.0; Regents of the University of California, 1998, 1-120 Edited by Todd Ewing.

Drenth, J., "Principles of Protein X-Ray Crystallography", Springer-Verlag, Aug. 30, 1995, p. 16.

Eck et al., "The structure of human lymphotoxin (Tumor Necrosis Factor-β) at 1.9-A resolution", J. Biol. Chem, Feb. 5, 1992, 267(4), 2119-2122.

Eck, M.J. et al., "The structure of tumor necrosis factor-α at 2.6 a resolution", J. Biol. Chem, Oct. 15, 1989, 264(29), 17595-17605.

Ellis, J., "Allosteric binding sites on muscarinic receptors", Drug Development Research, Feb. 1997, 40(2), 193-204.

Gomez et al., "Thermodynamic mapping of the inhibitor site of the aspartic protease endothiapepsin", Journal of Molecular Biology, Sep. 22, 1995, 252(3), 337-350.

(Continued)

*Primary Examiner* — Lori A Clow
(74) *Attorney, Agent, or Firm* — Woodcock Washburn, LLP

(57) ABSTRACT

Method of identifying compounds that modulate intermolecular interactions between a target protein and a modifier are disclosed. Pharmaceutical composition comprising compounds that inhibit intermolecular interactions between a target protein and a modifier are disclosed. Methods of treating individual suffering from inflammatory conditions, undesirable immune responses, immunological conditions and bacterial infections are disclosed.

5 Claims, 4 Drawing Sheets

OTHER PUBLICATIONS

Good et al., "New molecular shape descriptors: application in database screening", J Comput Aided Mol Des., Feb. 1995, 9(1), 1-12.
Goodsell, D.S. et al., Automated docking of flexible ligands: Applications of autodock, J. Mol. Recogn., Jan.-Feb. 1996, 9(1), 1-5.
Gschwend et al., "Molecular docking towards drug discovery" J. Mol. Recogn., Mar.-Apr. 1996, 9(2), 175-186.
Hansen et al., "Re-examination and further development of a precise and rapid dye method for measuring cell growth/cell kill", Journal of Immunological . Methods, May 12, 1989, 119(2), 203-210.
Hilser et al., "Structure-based calculation of the equilibrium folding pathway of proteins. Correlation with hyrdogen exchange protection factors", J. Mol Biol., Oct. 11, 1996, 262(5), 756-772.
Huang & Korngold, "Immunoglobulin superfamily proteins: structure, mechanisms, and drug discovery", Biopolymers., 1997; Epub: Dec. 6, 1998, 43(5), 367-382.
Iversen et al., "Characterization of the allosteric binding pocket of human liver fructose-1-6-bisphosphatase by protein crystallography and inhibitor activity studies", Protein Science, May 1997, 6(5), 971-982.
Kellogg & Abraham, "Key, Lock, and Locksmith: complementary hydropathic map predictions of drug structure from a known receptor-receptor structure from known drugs", J Mol Graph, Dec. 1992, 10(4), 212-217, 226.
Kleywegt et al., "detection, Delineation, Measurement and Display of Cavities in Macromolecular Structures", Acta Cryst., Mar. 1, 1994, 50(Part 2), 178-185.
Kollias-Baker et al., "Agonist-indepandant effect of an allosteric enhancer of the A1 Adenosine receptor in CHO cells stably expressing the recombinant human A1 receptor", Journal of Pharmacology. Experimental Therapeutics, May 1997, 281(2), 761-768.
Kundrot & Evans, "Designing an allosterically locked phosphofructokinase", Biochem, Feb. 12, 1991, 30(6), 1478-1484.
Kuntz, I, "Structure-based strategies for drug design and discovery", Science, Aug. 21, 1992, 257(5073), 1078-1082.
Ladjimi et al., "Structure-function relationship in allosteric aspartate carbamolyltransferase from *Scherichia coli* II. Involvement of the C-Terminal Region of the regulatory chain in homotropic and heterotropic interactions", J. Mol Biol., Dec. 20, 1985, 186(4), 715-724.
Langridge et al., "Real-time color graphics in studies of molecular inetractions", Science, Feb. 13, 1981, 211(4483), 661-666.
Li et al., "A computer screening approach to immunoglobulin superfamily structures and interactions: Discovery of small non-peptidic CD4 inhibitors as novel immunotherapeutics", Proc Nat'l Acad Sci. U.S.A., Jan. 7, 1997, 94(1), 73-78.
Low et al., "Phycomycosis of the kidney associated with a transient immune defect and treated with clotrimazole", J Urol., Jun. 1974, 111(6), 732-734.
Murali & Greene, "Structure-based design of immunologically active therapeutic peptides", Immunol Res, Jan. 1998, 17(1-2), 163-169.
Ozaita et al., "inhibition of monoamine oxidase A and B activities by imidazol(ine)/guanidine drigs, nature of the interaction and distinction from I2-imidazoline recepotrs in rat liver", British Journal of Pharmacology, Jul. 1997, 121(5), 901-912.
Piatier-Tonneau et al., "Interaction of CD4 with HLA class II antigens and HIV gp120", Immunogenetics, Aug. 1991, 34(2), 121-128.
Robichon et al., "A partial agonist model used in the allosteric modulation of the NMDA receptor, " European Journal of Pharmacology., Jun. 11, 1997, 328(2-3), 255-263.
Service, R. F., "Structural Genomics: Tapping DNA for Structures Produces a Trickle", Science, Nov. 1, 2002, 298(5595), 948-950.
Shoichet & Kuntz, "Protein docking and complementarity", J. Mol. Biol., Sep. 5, 1991, 221(1), 327-346.
Sobolev et al., Molecular docking using surface complementarity, Proteins, May 1996, 25(1), 120-129.
Strynadka et al., "Molecular docking programs successfully predict the binding of a β-lactamase inhibitory protein to TEM-1 β-lactamase", Nat Struct. Biol., Mar. 1996, 3(3), 233-239.
Takasaki et al., "Structure-based design and characterization of exocyclic peptidomimetics that inhibit TNF alpha binding to its receptor", Nat Biotechnol, Nov. 1997, 15(12), 1266-1270.
Tang et al., "Rational design of allosteric ribozymes" Chemistry & Biology, Jun. 1997, 4(6), 453-459.
Tijane et al., "Conformational modification of mscle phosphofructokinase from *Jaculus orientalis* upon ligand binding", FEBS Lett., Mar. 13, 1989, 245(1-2), 30-34.
Wu & Thompson, "Selective medium for *Pseudomonas cepacia* containing 9-chloro-9-(4-diethylaminophenyl)-10-phenylacridan and polymyxin B sulfate", Appl Environ Microbiol., Oct. 1984, 48(4), 743-746.
Xie et al., "Thermodynamic characterization of an equilibrium folding intermediate of staphylococcal nuclease", Protein Science, Dec. 1994, 3(12), 2175-2184.
Zographos et al., "The structure of glycogen phosphorylase b with an alkyldihydropyridine-dicarboxylic acid compound, a novel and potent inhibitor", Structure, Nov. 15, 1997, 5(11), 1413-1425.
Ghuysen et al., "Molecular structures of penicillin-binding proteins and β-lactamases" Trends in Microbiology, Oct. 1, 1994, 2(10), 372-380.
Strynadka et al., "Structure-based design of a potent transition state analogue for TEM-1 β-lactamase" Nature Structural Biology, Aug. 1996, 3(8), 688-695.

CAVITY INDUCED ALLOSTERIC MODIFICATION OF INTERMOLECULAR INTERACTIONS AND METHODS OF IDENTIFYING COMPOUNDS THAT EFFECT THE SAME This application is a continuation of application Ser. No. 09/720,647, filed on Jul. 17, 2001, now U.S. Pat. No. 7,653,495, which is a U.S. national stage application of PCT/US99/15062, filed on Jul. 1, 1999, which claims priority to provisional applications 60/091,431 filed on Jul. 1, 1998 and 60/133,435 filed on May 11, 1999. Each of the foregoing applications is incorporated by reference herein in its entirety.

This application claims priority to provisional application Ser. No. 60/091,431, filed Jul. 1, 1998 and Ser. No. 60/133,435, filed May 11, 1999, which both have the same title as this application and which are both incorporated herein by reference.

ACKNOWLEDGMENT OF GOVERNMENT RIGHTS

The present invention was made under Grant 1R21RR13360-01 from the National Institutes of Health. The Government may have certain rights to the invention.

This invention was made with government support under NIH-IRs: RES970326-1020 and RES990113-1353, and Grant Nos.: 5-R01-EY-09332 and 1R21RR13360-01 awarded by the National Institutes of Health. The government has certain rights in the invention.

FIELD OF THE INVENTION

The present invention relates to the identification of compounds that modulate intermolecular interactions by allosterically modifying a functionally critical site of a protein involved in such interactions and to methods of identifying the same.

BACKGROUND OF THE INVENTION

One of the challenges in the development of therapeutic compounds is to find a small molecule that is able to mediate a desired biological effect. Traditionally, synthetic chemistry and natural product screening have been the principal means for the derivation of many drug products.

High-throughput random screening is a standard procedure adopted by pharmaceutical companies for the discovery of lead compounds. This method relies upon availability of a large chemical database of natural/medicinal products. This procedure does not require the knowledge of principle components of biomolecules that cause disease. In short, it is a blind process to screen therapeutic lead compounds. The advantage of this approach is that it facilitates to build a large medicinal chemical database and can be repeatedly used to screen therapeutic compounds. Unfortunately, random screening is tedious and often requires isolation and characterization from natural extracts. Natural products are complex and include the stereochemical complexities inherent in their natural origin.

While high-throughput random screening procedures have been used to identify some novel therapeutic molecules, such procedures are often limited by the availability of large chemical databases. Advances in computer technology and the understanding of protein-protein interactions has allowed for attempts to replace the high-throughput screening procedures with computer-aided analysis and design of novel molecules. Such structure based approaches have reduced the time and resources to discover novel compounds.

Structure based approaches have been used to develop several inhibitors that are either "substrate analogs" or "allosteric" inhibitors. Allosteric effectors, in some cases, are considered superior to conventional substrate analog for reasons: (1) it is non-competitive with natural ligand, (2) it can be effective at a lower concentration, (3) allosteric binding sites are less conserved and thereby specificity and selectivity can be enhanced, and (4) in some cases allosteric effectors can inhibit the target molecules' function by trapping it in an intermediate non-native or molten globular state.

Structure-based approaches represent a targeted pathway where therapeutic agents are designed towards the biomolecule responsible for disease. There are two major approaches in the design of lead therapeutic compounds based on the nature of the molecule. For enzymes, design of substrate analogs (from the knowledge of active site) and peptidomimetics that has shown promise in some cases.

Substrate analogs are developed to compete with the natural substrate and occupy the active site. Thus, a potent therapeutic compound must have high affinity, exhibit selectivity and have longer retention time. Substrate analogs are better suited for enzymes, because many receptors and other non-enzyme molecules, such as receptors and their ligands have no defined active site but alter biological function. In such cases, a peptide's ability to mimic a protein's local structural features is one of the ways used to design therapeutic compounds. Substrate analog interactions are often not reversible.

Peptidomimetics are developed both as therapeutic agents and as a probe to understand biological functions. Natural products targeting opioid and hormone receptors are historical examples of peptidomimetics because they validate many of the concepts invoked in rational design. These compounds provide a classic example of how structurally different non-peptides may be from their peptide parents (lacking flexibility, amide bonds and obvious pharmacophore similarity) and how their modification can lead to highly selective ligands for subtypes of receptors for both peptide and non-peptide compounds.

Elucidation of the conformation of a peptide can provide insights about the structural requirements of its binding to a receptor (Boteju, L. W. et al., 1996, J. Med. Chem., 39:4120-4; and Cho, M. J. et al., 1996, Trends in Biotechnology, 14:153-8; which are both incorporated herein by reference). A major problem, however, in structure-activity studies of linear peptides is the large degree of flexibility, not only of the side-chain residues, but also of the peptide backbone. Substitution of individual amino acids followed by biological screening might reflect affective differences on structure rather than on residues implicated in binding. Consequently, spectroscopic studies in solution, where a rapid equilibrium between numerous conformations is likely to occur, have had little impact on the design of linear peptide analogues. In contrast, constrained peptides delineate solution conformations for correlation with receptor bound conformations. Bioactive compound design based upon conformational constrained peptide analogs representative of the recognition elements of the protein constitutes an effective approach to mimetic drug design. Constraints imposed upon peptides to lock in a particular conformation often times emulate those imposed by the tertiary structure of protein ligands. Imposed constraints can reflect the use of amino acids that contribute to the propensity of a particular secondary structure such as amphipathic helical repeats.

Despite the diverse usefulness of peptidomimetics, they remain less viable drugs due to their poor bioviability. Nevertheless, active peptide analogues with modified bonds or side chains, provide another approach in defining bioactive conformations and are valuable pharmacological probes, because generally they are more resistant to proteolytic degradation.

Protein structures have been elucidated using crystallography, NMR and molecular modeling. The three dimensional structures of proteins reveal (1) overall folding of the molecule, (2) scaffolds: secondary structural features such as α-helix, β-sheet, (3) functional units; b-turns and loops, and (4) surfaces that include cavities, clefts, pockets and crevices formed by the folding of amino acid chains on itself and, in the case of multimeric protein complexes, on itself and the amino acid chains of other subunits. Cavities, clefts, pockets and crevices can accommodate water molecules within an interior. Depending upon the nature of the amino acids which form the cavities, clefts, pockets and crevices molecules, the interior of these structural features have specific chemical and electrostatic properties as well as spatial dimensions.

Determination of crystal structures of proteins/receptors have provided a basic understanding of protein/receptors' function. Several receptors such as EGF receptors are activated either by ligands or by association with other erbB family of receptors. One of the hypothesis is that conformational changes induced either by ligand or by co-receptors elicits signal transduction. Thus, it is presumed that through allosteric mechanisms receptors can modulate signal transduction. Allosterically driven biological functions are also known both in enzymes and receptors (Ellis, J., 1997, Drug. Dev. Res., 40:193-204, and Kundrot, C. E. et al., 1991, Biochem., 30:1478-1484, which are both incorporated herein by reference). Attempts to modulate the function of proteins/receptors have been made and often referred to as "allosteric modification or allosteric inhibitors".

Allosteric modification is a well known technique that has been studied in several enzymes (Iverson, L. F. et al., 1997, Protein Science, 6:971-982; Ladjimi, M. M. et al., 1985, J. Mol. Biol., 186:715-724; Ozaita, A. et al., 1997, Brit. J. Pharm., 121:901-912; Tang, J. et al., 1997, Chemistry & Biol., 4:453-459; and Tijane, M. et al., 1989, FEBS Lett., 245:30-34; which are each incorporated herein by reference) and receptors (Berthold, M. et al., 1997, Neurochem. Res., 22:1023-1031; Ellis, J., 1997, Drug. Dev. Res., 40:193-204; Kolliasbaker, C. A. et al., 1997, J. Pharmco. Exp. Therap., 281:761-768; and Robichon, R. et al., 1997, Eur. J. Pharmco., 328:255-263 which are each incorporated herein by reference). Hitherto techniques often used mutagenesis or small molecules identified from screening. Allosteric modifications have been used in enzymes to alter the enzymes' kinetics and in some cases used to develop inhibitors.

There is a need for modulators of intermolecular interactions and for methods of identifying such modulators. There is a need for inhibitors of intermolecular interactions and for methods of identifying such inhibitors. There is a need for enhancers of intermolecular interactions and for methods of identifying such enhancers. Structure based ligand design, as practiced today, requires the knowledge of cavity of known functions such as active sites, or cavities identified by high throughput (ligand binding). There is a need for a generalized approach to identify functional cavities for novel ligand design.

SUMMARY OF THE INVENTION

The present invention relates to methods of identifying compounds that modulate intermolecular interactions between a protein target and a modifier. Modulators may be inhibitors, i.e. compounds that inhibit intermolecular interactions, or enhancers, i.e. compounds that enhances intermolecular interactions. According to the methods of the present invention, a cavity, cleft, pocket or crevice in the protein target which is proximal to a functionally critical site of the target protein involved in intermolecular interactions with the modifier is identified that may be distinct and proximal from the catalytic site. The volume of the cavity, cleft, pocket or crevice is calculated and its chemical and electrostatic properties are mapped. Functional groups and compounds are identified which can be accommodated by the cavity, cleft, pocket or crevice. The parameters for identifying such functional groups and compounds include size, charge and hydrophobicity/hydrophilicity characteristics. Compounds which contain functional groups that can be accommodated by the cavity, cleft, pocket or crevice, including compounds which can be completely accommodated by the cavity, cleft, pocket or crevice, are then tested in an in vitro assay to determine whether they modulate target-modifier interactions.

The present invention relates to pharmaceutical compositions and methods of treating an individual suffering from an inflammatory condition.

The present invention relates to pharmaceutical compositions and methods of treating an individual suffering from an undesirable immune response or immunological condition are disclosed.

The present invention relates to pharmaceutical compositions and methods of treating an individual suffering from a bacterial infection are disclosed.

BRIEF DESCRIPTION OF THE FIGURES

FIG. 1A shows the disposition of cystine-knot loops (WP9) and a cavity near the binding site. The portion of the molecule denoted with an arrow shows the loop that was used as a template to design peptidomimetic. FIG. 1B shows inhibition of TNFα-induced cytolysis of L929 cells by the antagonistic peptides. Absorbance obtained with 1 mg/ml of ACT-D alone and with ACT-D and 50 pg/ml of TNFα were considered as 100% survival and 100% cytotoxicity, respectively. The results indicate the means and standard deviations derived from three independent experiments.

FIG. 2A depicts the WP9 cavity of TNF receptor. FIG. 2B shows the molecule s7 forms a complex with a binding energy of −40 Kcal/mol without any chemical optimization. Since this compound is not chemically altered for maximal binding, kinetics of ligands have not been performed. FIG. 2C shows results when tested in an apoptosis assay similar to the peptidomimetics, i.e. about 20% protection at 300 μM concentration.

DETAILED DESCRIPTION OF PREFERRED EMBODIMENTS

Figure 1A:
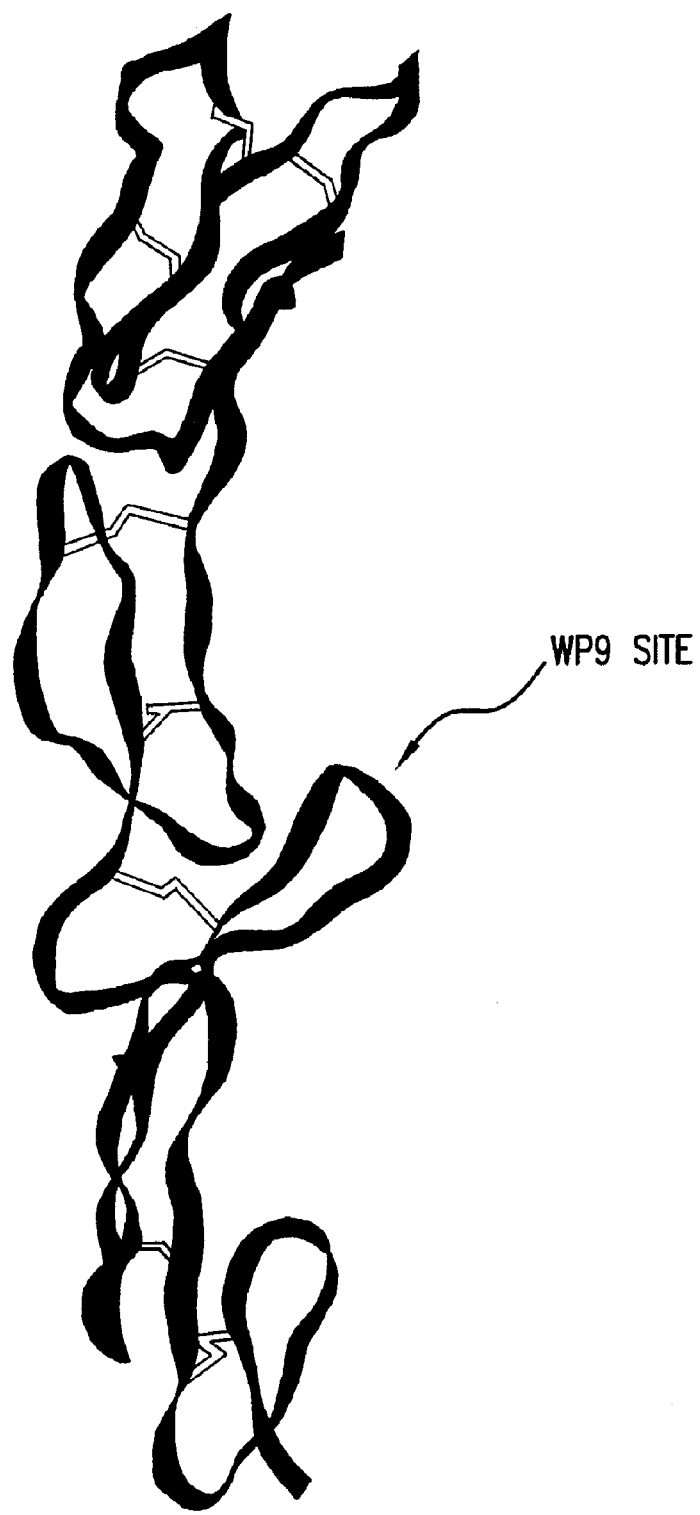
FIGS. 1A and 1B depict the structure of third domain of TNF receptor.

As used herein, the term "target protein" is meant to refer to a protein that is involved in intermolecular interactions with a modifier. The target protein may be a cellular protein or a protein that exists outside of a cell. The target protein may be, for example but without limitation to, a membrane bound protein, a cytosolic protein, a nuclear protein, an enzyme, a cytokine, a lymphokine, a chemokine, an adhesion molecule, a growth factor, or a receptor for such proteins. In some embodiments, the target protein is tumor necrosis factor (TNF) receptor family including TNF receptors, fas, CD40.

gp30, and fas ligand, TNFα, CD4, β-lactamase, c-erbB2 p185 translation product, growth hormone receptor, growth hormone, insulin receptor, insulin, IL-1 receptor, IL-1, IL-2 receptor, IL-2, epidermal growth factor receptor (EGFR), and epidermal growth factor (EGF). A target protein must have a cavity, cleft groove pocket of crevice as part of its three dimensional structure.

As used herein, the term "modifier" is meant to refer to a compound which is involved in intermolecular interactions with a target protein. The modifier may a proteinaceous molecule such as a protein, polypeptide or peptide, or a non-proteinaceous molecule such as a sugar, polysaccharide, nucleic acid molecule, or other non-proteinaceous organic or non-organic molecule. The term modifier may be used interchangeably herein with the term "ligand". Examples of proteinaceous modifiers include: proteins such as membrane bound proteins, cytosolic proteins, and nuclear proteins; and proteins, polypeptides and peptides such as proteinaceous enzyme substrates, cytokines, lymphokines, chemokines, adhesion molecules, growth factors, or receptors for such molecules. In some embodiments, the modifier is (TNF) receptor family including TNF receptors, fas, CD40. gp30, and fas ligand, TNFα, CD4, β-lactamase, c-erbB2 p185 translation product, growth hormone receptor, growth hormone, insulin receptor, insulin, IL-1 receptor, IL-1, IL-2 receptor, IL-2, epidermal growth factor receptor (EGFR), and epidermal growth factor (EGF).

As used herein, the term "intermolecular interactions" is meant to refer to interactions that occur between and protein, which is referred to as the target protein, and a second molecule, which is referred to as a modifier. The interactions occur at a site on the target protein referred to as the target protein:modifier interaction site. Intermolecular interactions include for example: association, oligomerization, binding, and conformational/structural perturbances. The intermolecular interaction between the target protein and the modifier results in some biological activity, the enhancement or inhibition of which is desirable in some circumstances. Examples of intermolecular interactions which result in a biological activity include processing of substrates by enzymes, ligand induced signal transduction, allosteric modulators, signal transduction due oligomerization, and protein small molecule binding (antagonists/agonists).

As used herein, the term "target protein:modifier interaction site" is meant to refer to the location on the target protein in which interaction between the target protein and the modifier occurs. In examples where the target protein is an enzyme and the modifier is an enzyme substrate, for example, the target protein:modifier interaction site is also referred to as the catalytic site. In examples where the target protein is a receptor, for example, the target protein:modifier interaction site is also referred to as the binding site. In some cases, such as when the target protein is a member of the immunoglobulin superfamily, the target protein:modifier interaction site may include complementarity determining regions (CDRs) or loops, which define the portions of the target protein which interact directly with modifier.

As used herein, the terms "cavity", "cleft", "pocket", "groove" and "crevice" are used interchangeable and are meant to refer to a molecular surface or location on a target protein that can accommodate at least one solvent such as for example water molecules, although some cavities may not be solvated. The identification process involves using molecular models in which a spherical probe of radius 1.4 A, which is approximate to a water molecule, is used to track the surface of the molecule. A cavity, can accommodate a water molecule, i.e. the probe that is the equivalent size of a water molecule can fit within the cavity. Accordingly, a cavity has dimensions and a volume which can be measured.

As used herein, the term "functionally critical site" is meant to refer to a site or region or location or secondary structural element on a target protein that is involved in either altering or mediating a function, the modulation of which is desirable. According to some embodiments of the invention, the function can be processing of a modifier that is an enzyme substrate by a target protein that is an enzyme, the functionally critical site is a target protein:modifier interaction site that is a catalytic site, and the desirable modulation is the inhibition of substrate processing by the enzyme. According to some embodiments of the invention, the function can be binding of the modifier to the target protein, the functionally critical site is a target protein:modifier interaction site that is a binding site, and the desirable modulation is the inhibition of target protein-modifier binding. Other examples of functionally critical sites include surfaces of a target protein which interface with an oligomer and loops that stabilize oligomers.

As used herein, the term "proximal" is used interchangeably with the term "adjacent to" and is meant to refer to the distinct locations of the cavity and a functionally critical site which is at a measurable distance. According to the invention, the cavity is at a distinct location from the functionally critical site. The two locations are distinct from each other so that the modification of the functionally critical site that occurs when a functional group of a compound occupies the cavity is allosteric modification. A cavity is proximal to a functionally critical site if the functionally critical site can be altered by molecular interactions between the target protein and at least a functional group of a compound which can be accommodated by the cavity. In preferred embodiments, a cavity that is proximal to a functionally critical site is generally within about 15-20 Angstroms to the functionally critical site.

As used herein, the term "modulate" is meant to refer to an effect upon intermolecular interactions may be caused by compounds according to the invention which allosterically modify molecular surfaces involved in such intermolecular interactions. Such compounds are referred to herein as "modulators". In some embodiments, the effect caused by a modulator may be the inhibition of intermolecular interactions, in which case the modulator is an "inhibitor". In some embodiments, the effect caused by a modulator may be the enhancement of intermolecular interactions, in which case the modulator is an "enhancer".

According to the invention, modulators, such as inhibitors or enhancers, of intermolecular interactions may be identified or designed to allosterically modify molecular surfaces involved in such intermolecular interactions. Thus, any intermolecular interactions between a target protein that has a cavity proximal to a functionally critical site such as a binding site or catalytic site, and a second molecule, a modifier which may or may not be a protein can be affected using compounds identified according to the invention.

The invention comprises a series of steps including: 1) identifying a cavity proximal to a functional critical site; 2) determining physical parameters of the cavity, 3) identifying functional groups which can be accommodated by the cavity; and 4) testing compounds which comprise such functional groups in an in vitro assay to determine whether such compounds are active.

According to the invention, the target protein must interact with a modifier and have a cavity proximal to a functional site. By identifying functionally critical sites and cavities of a target protein or modifier, which can be done routinely, it has been discovered that such cavities, if proximal to the functionally critical site, can be targets for compounds that can modulate the activity of the target protein with respect to its interaction with modifiers. Since the interaction with modifiers is necessary for a specific biological function attributed to the target protein, inhibition of target protein:modifier interaction inhibits the biological function associated with such interaction. Likewise, the enhancement of target protein: modifier interaction may enhance the biological function associated with such interaction.

The means to identify functionally critical sites on a target protein are numerous, varied and well known. For example, the identification of active or catalytic sites of enzymes, and the binding sites of receptors or ligands are well known. The functionally critical site of a target protein may be identified several different ways including, but not limited to: by identification of β-factors on the target protein structure as imaged using crystal or nuclear magnetic resonance (NMR) images either by thermal β-factors on the atoms of target protein from crystal structure or flexible loops inferred from NMR signals, or microcalorimetric analysis of complex or mutation analysis of molecule; by protein, peptide or peptidomimetic mapping of the target protein including immunomapping; and by identifying CDRs on the target protein structure. β-factors are parameters that define flexibility such as thermal parameters from crystallographic studies. Thermal β-factors are parameters that reflect the disordered (flexible) nature of atoms in the 3D structure determined by X-ray diffraction. When the structures are determined by X-ray diffraction, the data needed to determine β-factors are measured as diffracted intensities. Fourier transform analysis of these data reveal the β-factors associated with the atoms in the molecule and β-factors always determined as a part of the crystal structure analysis. These β-factors reflect the disorder or flexibility of the atoms in the molecule. Calorimetric values from thermodynamic studies can also be used to identify functionally critical site of a target protein. An algorithm has been described which is also useful to identify mobile regions. This algorithm and its use are described in Daquino, J. A. et al., 1996, Proteins, 25:143-156; Gomez, J. et al., 1995, Journal of Molecular Biology, 252:337-350; Hilser, V. J. et al., 1996, J. Mol. Biol., 262:756-772; and Xie, D. et al., Protein Science, 3:2175-2184; which are each incorporated herein by reference.

The cavity of the target protein may be identified by any of several well known techniques including, but not limited to, crystal structure analysis, NMR and computer models. The cavity size must be able to accommodate at least one water molecule. The techniques for identifying cavities on the surface of proteins are well known and described for example in "*Protein Engineering*", Edited by Dale L. Oxender, C. Fred Fox, Liss Co., New York (1987) (for crystallography & NMR) and "*Guidebook on Molecular Modeling in Drug Design*", Edited by N. Claude Cohen, Academic Press, 1996 San Diego, Calif. (1996) (for computer modeling), which are each incorporated herein by reference. To determine whether a surface can accommodate water, using the computer model of the protein, the surface is probed with small sphere of radius 1.4 Å, a size similar to that of a water molecule. The atoms touched by the probe sphere are marked as surface atoms. Mapping the surface atoms as a continuous surface defines the geometry of the surface. The geometry then allows one to classify cavities. To be proximal the cavity must not be at the same location as the functionally critical site.

Once a cavity that is proximal to the functionally critical site is identified, certain physical parameters are ascertained. Such parameters include at least one and preferably more than one of the following: the volume and dimensions of the cavity are measured or otherwise calculated; the electrostatic properties of the cavity and/or the chemical properties, i.e. hydrophobicity/hydrophilicity, of the cavity may be mapped. The interior of the cavity is thus defined by the volume and dimensions of the interior of the cavity and/or the map of electrostatic properties within the interior of the cavity and/or the map of chemical properties within the interior of the cavity.

In some embodiments, the volume and dimensions of the interior of the cavity can be determined by rolling a probe radius of 1.4 Å (equivalent of one water molecule) to generate a surface. The accessible surface is then calculated using among many other programs freely available the program MS (Michael S. Connolly). MS is available from QCPE (QCPE, Creative Arts Bldg., 181, Indiana University, Bloomington, Ind. 47405) for and also packaged in several graphic software such as INSIGHT and QUANTA (both available from Molecular Simulations, Inc. San Diego, Calif.). In addition, the program described in Kleywegt, G. J. et al., 1994, Acta, D50:178-185, which is incorporated herein by reference, can also be used to detect, measure and characterize cavities.

The electrostatic properties and chemical properties, i.e. hydrophobicity/hydrophilicity, of the cavity can be mapped. The residues in the binding region are analyzed for site-points (atoms that are capable of forming hydrogen bonds, hydrophobic interactions) using the program GENSITES. Other equivalent programs such SPHGEN which is part of DOCK can also be used. The DOCK program is available from Prof. Kuntz laboratory, University of California at San Francisco, San Francisco Calif. The program identifies possible locations based upon differences in surface accessibility of different sized spheres rolling over the molecular surface of the target protein. A three dimensional map of the interior of the cavity is generated which corresponds to the dimensions, charge and chemical properties of the interior surfaces.

Once physical parameters of the cavity are ascertained, functional groups are identified which can be accommodated by the cavity. Such functional groups must be of an appropriate size such that they can fit within the interior of the cavity. Additionally, functional groups must be electrostatically and chemically compatible with interior of the cavity. That is, the functional group must have electrostatic properties and chemical properties which would result in forces that attract the functional group to the interior of the cavity rather than repelling forces which would inhibit or prevent the functional group from occupying the interior of the cavity. Using the site points developed in the cavity, possible molecular fragments are identified using the program LUDI. LUDI is part of INSIGHT which is available from Molecular Simulations, Inc. Another program from QUANTA called CAVEAT, also available from Molecular Simulations, Inc., can be used to identify functional groups which can be accommodated by the cavity.

In some preferred embodiments, shape complementarity is used as initial screen for detecting fragments with different moieties. The molecular modeling approach assumes that the site is relatively rigid and that the intramolecular energy change upon target protein/modulator binding is small compared to the interaction energy between target protein/modifier conformations. Therefore, the binding mode specifies which molecular point (expressible as Cartesian coordinates) on the modulator should be bound to which site point (also Cartesian coordinates) at the binding site. The fitting procedure is tantamount to identifying common surface features with subsequent docking of complementary surfaces.

Docking between two complementary surfaces can be an exhaustive procedure even with known topography. First, a probe sphere is rolled on the binding surface as the locus of the possible positions which can be occupied by the atoms of the binding molecule. This continuum of loci can be reduced to a set of discrete points localized at each residue and assigned a type. An additional type assignment for each site point is given depending on the relative geometric description of this residue with its three closest neighbors. These points define regions for fitting fragments identified in the LUDI data base. Complexes are subjected to energy minimization and molecular dynamics calculations to optimize the relative orientations and to monitor conformational changes in the target protein that are induced upon complex formation. This procedure is done using AUTODOCK (Goodsell, et al. 1996 which is incorporated herein by reference) and LIGIN (Sobolev, et al. 1996 which is incorporated herein by reference) or any other equivalent programs that use docking algorithms. These two methods allow exploration of both conformational flexibility and possible chemical modification for enhanced binding properties. This approach provides an estimate of the size of the molecule that can bind and identify possible functional groups that can interact with neighboring residues and provides a way to develop novel molecular structures based on the distribution of site points.

Novel molecular compounds based on site points may encounter difficulty in synthesis and suitability for biological assays. To overcome this obstacle, large three-dimensional chemical structure databases (MDL Corp., San Leandro, Calif.) are searched to identify compounds (Good, A. C. et al., 1995, J. Comput. Aided Mol. Des., 9:1-12; Kuntz, I. D., 1992, Science, 257:1078-1082; and Li, S. et al., 1997, Proc. Natl. Acad. Sci. U.S.A., 94:73-78; which are each incorporated herein by reference). The advantage of using the chemical database is two fold: (1) it offers a unique opportunity to search for novel molecules to small fragments that can be easily incorporated in a larger compound and (2) selection of chemical compounds is facilitated from the knowledge of their availability, synthetic pathway, toxicity, and solubility etc. Currently, the three-dimensional structure chemical database contains about 250,000 small molecules. Therapeutically useful compounds can be identified in the chemical databases using the DOCK (Good, A. C. et al., 1995, J. Comput. Aided Mol. Des., 9:1-12 and Goodsell, D. S. et al., 1996, J. Mol. Recogn., 9:1-5, which are both incorporated herein by reference) algorithm. The cavity is explored with each small molecule from the database for maximal interaction such as hydrophobic, hydrogen bonds and complement electrostatic properties by conformational search. Based on the binding energy, the molecules are ranked and, for example, the top 200 compounds are selected. In addition, molecules similar to the one constructed from de novo ligand design can be identified in the databases using a three-dimensionally constrained fragment search. The short listed molecules obtained both by database search (DOCK) and fragment search are used to create a small chemical database library using MDL's project library software. Quantitative Structure Activity Relation (QSAR) analysis in medicinal chemistry and pharmacology has proven useful in making predictions for molecules that are chemically similar to those of the original data set. Distance geometry directed QSAR allows for testing of a much wider class of compounds due to its independence from physico/chemical parameters. The molecules in the library are compared for a common motif and analysis similar to 3D-QSAR are carried out using ASP and TSAR (Oxford Molecular, Oxford, England) sequentially to find the suitable functional groups for maximal binding energy.

Following identification, compounds selected by one of the various approaches or combinations thereof are evaluated for biological activity in an in vitro assay to determine whether they modulate target-modifier interactions. Biological assays are utilized for which intermolecular interactions are known to result in a detectable signal or phenotype or for which it is known that inhibition of intermolecular interactions result in a detectable signal or phenotype. Using such assays, comparative assays are performed in the presence or absence of the identified compounds to confirm biological activity of the compound.

Pharmaceutical compositions according to the invention include components identified by the methods of the invention which further comprise a pharmaceutically acceptable carriers or vehicles, such as, for example, saline. Any medium may be used which allows for successful delivery of the compound. One skilled in the art would readily comprehend the multitude of pharmaceutically acceptable media that may be used in the present invention. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions, such as injectable pharmaceutical compositions, are required to meet specific standards regarding sterility, pyrogens, particulate matter as well as isotonicity and pH, i.e. inter alia sterile, pyrogen-free and free of particulate matter.

Pharmaceutical compositions may be formulated by one having ordinary skill in the art with compositions selected depending upon the chosen mode of administration. Suitable pharmaceutical carriers are described in *Remington's Pharmaceutical Sciences*, 18$^{th}$ Edition, A. R. Gennaro, Ed., Mack Publishing Company, Easton, Pa., a standard reference text in this field, which is incorporated herein by reference.

The pharmaceutical compositions of the present invention may be administered by any means that enables the active agent to reach the agent's site of action in the body of a mammal. Pharmaceutical compositions may be administered parenterally, i.e., intratumor, intravenous, subcutaneous, intramuscular. Intravenous and intratumor administration are preferred routes. For example, in cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

EXAMPLES

Example 1

In one embodiment of the invention, CIAM technology is used to identify compounds that inhibit interactions between tumor necrosis factor (TNF) receptor and TNFα.

Tumor necrosis factor receptor is one of the first receptors to be studied at the atomic detail both as a complex and uncomplexed polypeptide. The crystal structure of the TNF receptor both in complexed and uncomplexed forms provides a general understanding by which these receptors bind to their ligands (Banner, D. et al., 1993, Cell, 73:431-45; Eck, M. J., et al. 1989, J. Biol. Chem., 264:17595-605; and Eck, M. J., et al. 1992, J. Biol. Chem., 267:2119-22; which are each incorporated herein by reference) and associated ligand induced conformational changes. The cystine knot in the TNF receptor family consists of 42 amino acid residues with 6 cystine residues forming three inter chain disulfide bond to create the structural motif. The three dimensional structure reveals the cystine-knots repeats about 30 Å in length are arranged in a head-to-tail fashion exposing the loops on one side of the receptor. These loops are either involved in oligomerization or ligand binding. Uncomplexed TNF receptors are observed as dimers. In the dimeric form, the first and last cystine domains involved dimeric contacts. The membrane proximal domain is disordered perhaps due to the lack of the transmembrane that normally holds this domain in a stable state. Crystal structure analysis of TNF receptor and TNFβ complex shows that there are three distinct binding sites, referred to as "WP5", "WP8" and "WP9".

To understand, the most energetically relevant binding sites, peptides were used as probes and several cyclic peptides were developed for species.

Figure 1B:
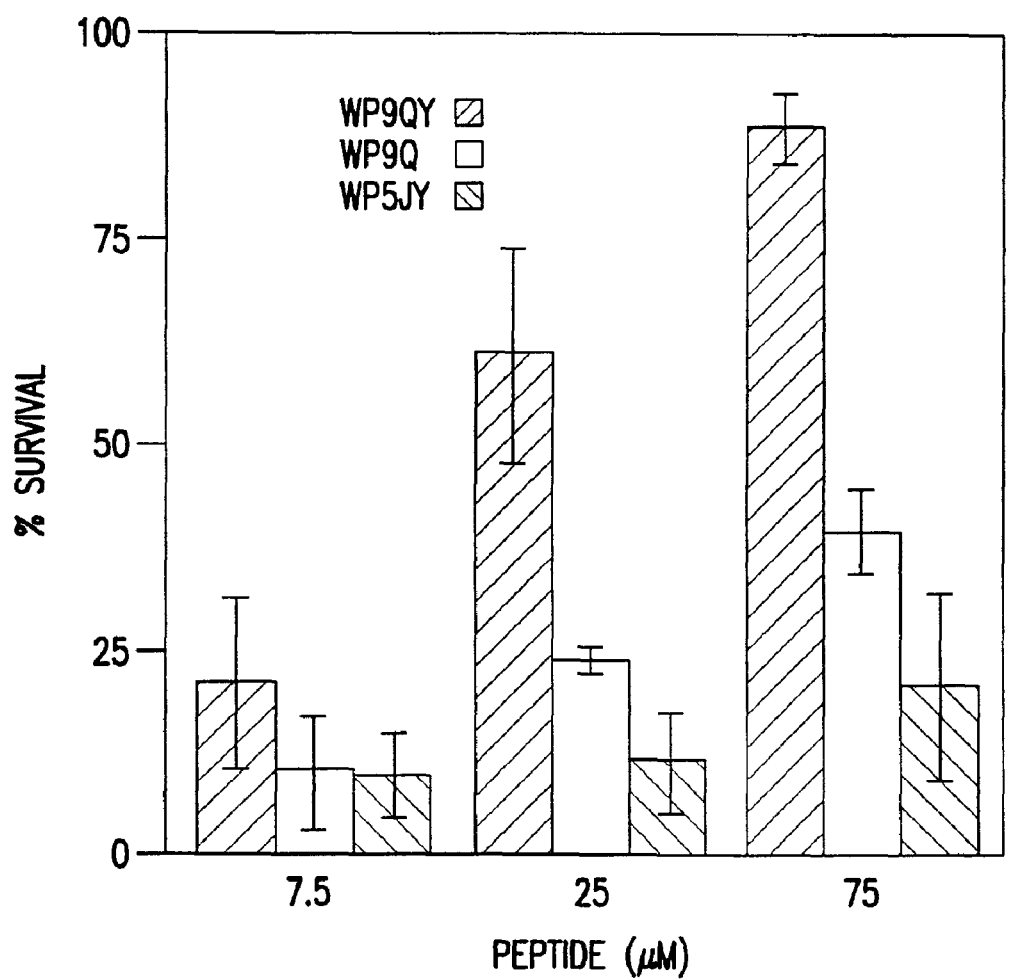

Peptidomimetics were developed and tested from all three surface loops of the TNF receptor: loop (56-73) of domain 1; loop (76-83) of domain 2 and loop (107-114) of domain 3 (FIG. 1A). The peptidomimetics are described in detail in Takasai, et al. 1997 Nature Biotechnology 15:1266-1270, which is incorporated herein by reference. The peptidomimetic engineered from the third domain (WP9QY) inhibited TNFα binding ($IC_{50}$=75 mM) to its receptor. Also, the peptidomimetic protected cells against TNFα induced cell death when apoptosis was induced with 7 pg of TNFα suggesting that the peptide specifically bind to TNFα. The peptidomimetic (WP9QY) is one of the first peptides to show anti-TNFα activity (FIG. 1B).

Figure 2A:
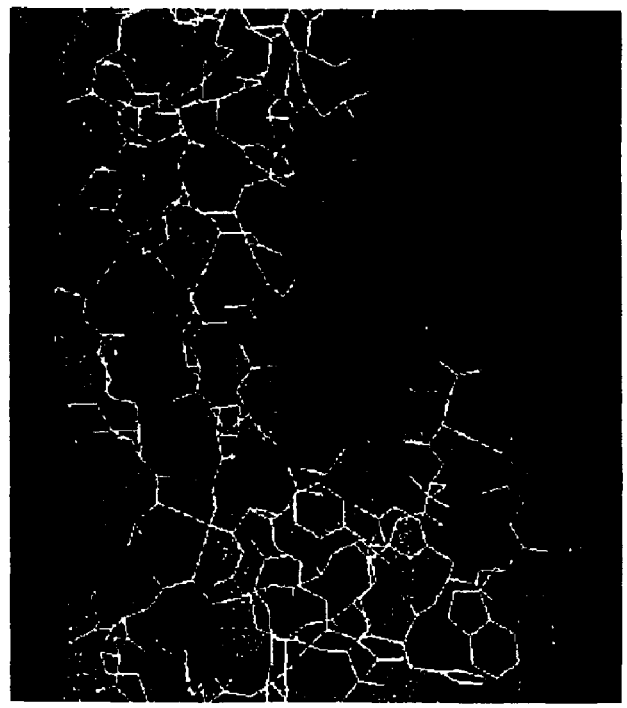
FIGS. 2A, 2B and 2C show a preliminary result from a small database search in the third domain of TNF receptor. For clarity, only the domain of the receptor is shown.
Figure 2B:
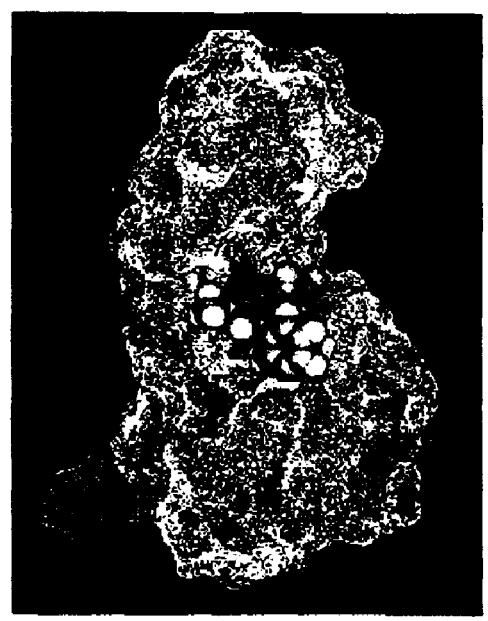
Figure 2C:
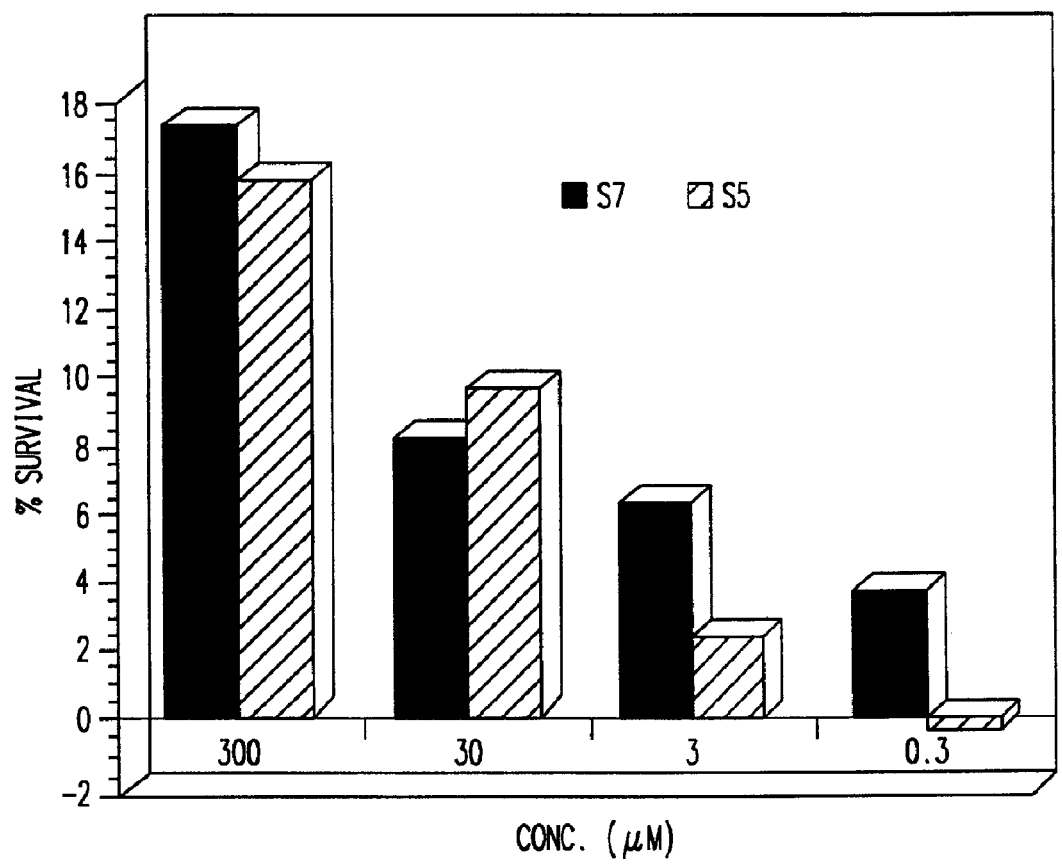

Based on the effect of the small loop in the third domain of TNF receptor identified by peptidomimetic analysis, a large cleft was identified that could be utilized for docking an allosteric inhibitor. The cavity is shallow: 8 Å deep, 17.6 Å long and 12.4 Å wide (FIG. 2A). The walls of the cavity are formed by residues involved in binding TNFα. The large cleft close to one of the binding sites (WP9) was used to perturb these loops by an allosteric effect, using a small molecule designed from the above procedures (DesJarlais, R. L. et al., 1986, J. Med. Chem., 29:2149-2153; DesJarlais, R. L. et al., 1988, J. Med. Chem., 3:722-729; Good, A. C. et al., 1995, J. Comput. Aided Mol. Des., 9:1-12; Gschwend, D. A. et al., 1996, J. Mol. Recogn., 9:175-186; Shoicet, B. K. et al., 1991, J. Mol. Biol., 221:327-346; Strynadka, N. C. et al., 1996, Nat. Struct. Biol., 3:233-239; and Strynadka, N. C. et al., 1996, Nat. Struct. Biol., 3:290-297; which are each incorporated herein by reference). About 232 structurally suitable molecules were selected from an initial screening of small chemical database built using MDL (MDL corporation, San Leandro, Calif.) structural chemical database containing about 10000 structures. Further analysis revealed that not all of them are conducive for biological experiments based on solubility and toxicity. For the purpose of testing, four compounds were tested for biological activity, but not for specificity and kinetics. The compounds were tested for apoptosis using a standard MTT assay (Hansen, M. B. et al., 1989, J. Immunol. Meth., 119:203-210, which is incorporated herein by reference). One compound, S7 with binding energy of −40 Kcal/mol (FIG. 2B) showed activity (FIG. 2C) in the MTT assay. These results indicate that small molecules can be developed as pseudo-allosteric inhibitors.

The present invention provides a novel strategy to modify the conformation of specific loops in an approach referred to as cavity induced allosteric modification (CIAM) between the target protein, TNF receptor, and the modifier, TNF. This strategy uses the known crystal structure of the TNF receptor. The surface of the target protein was generated by rolling a probe radius of 1.4 Å (equivalent of water molecule). The accessible surface was calculated using program MS (Connolly, M. L. et al., 1993, J. Mol. Graph, 11:139-141 and Langridge, R. et al., 1981, Science, 211:661-666, which are both incorporated herein by reference). The residues in the binding region are analyzed for site-points (atoms that are capable of forming hydrogen bonds, hydrophobic interactions) using the program GENSITES. which identifies possible locations based upon differences in surface accessibility of different sized spheres rolling over the molecular surface of the target protein. Using the site points developed in the cavity, possible molecular fragments were identified using the program LUDI (Bohm, L. W. et al., J. Mol. Recogn., 6:131-137 which is incorporated herein by reference). Shape complementarity was used as initial screen for detecting fragments with different moieties. The molecular modeling approach assumes that the site is relatively rigid and that the intramolecular energy change upon ligand/inhibitor binding is small compared to the interaction energy between receptor/protein conformations. Therefore, the binding mode specifies which molecular point (expressible as Cartesian coordinates) on the inhibitor should be bound to which site point (also Cartesian coordinates) at the binding site. The fitting procedure is tantamount to identifying common surface features with subsequent docking of complementary surfaces.

Docking between two complementary surfaces can be an exhaustive procedure even with known topography. However, one can reduce the dimensionality of the problem by computing site points on the binding surface. First, a probe sphere is rolled on the binding surface as the locus of the possible positions which can be occupied by the atoms of the binding molecule. This continuum of loci can be reduced to a set of discrete points localized at each residue and assigned a type. An additional type assignment for each site point is given depending on the relative geometric description of this residue with its three closest neighbors. These points define regions for fitting fragments identified in the LUDI data base. Complexes are subjected to energy minimization and molecular dynamics calculations to optimize the relative orientations and to monitor conformational changes in the ligand that are induced upon complex formation. This procedure is done using AUTODOCK (Goodsell, D. S. et al., 1996, J. Mol. Recogn., 9:1-5 which is incorporated herein by reference) and LIGIN (Sobolev, et al. 1996 Proteins, 25:120-129 which is incorporated herein by reference). These two methods allow exploration of both conformational flexibility and possible chemical modification for enhanced binding properties. This approach provides an estimate of the size of the molecule that can bind, identifies possible functional groups that can interact with neighboring residues, and provides a way to develop novel molecular structures based on the distribution of site points. Often, novel molecular compounds based on site points encounter difficulty in synthesis and suitability for biological assays.

To overcome this obstacle, large three-dimensional chemical structure databases (MDL Corp., San Leandro, Calif.) are searched to identify compounds (Good, A. C. et al., 1995, J. Comput. Aided Mol. Des., 9:1-12; Kuntz, I. D., 1992, Science, 257:1078-1082; and Li, S. et al., 1997, Proc. Natl. Acad. Sci. U.S.A., 94:73-78; which are each incorporated herein by reference). The advantage of using the chemical database is two fold: (1) it offers a unique opportunity to search for novel molecules to small fragments that can be easily incorporated in a larger compound and (2) selection of chemical compounds is facilitated from the knowledge of their availability, synthetic pathway, toxicity, and solubility etc. Currently, the three-dimensional structure chemical database contains about 250,000 small molecules. Therapeutically useful compounds can be identified in the chemical databases using the DOCK (Good, A. C. et al., 1995, J. Comput. Aided Mol. Des., 9:1-12 and Goodsell, D. S. et al., 1996, J. Mol. Recogn., 9:1-5, which are both incorporated herein by reference) algorithm. The cavity is explored with each small molecule from the database for maximal interaction such as hydrophobic, hydrogen bonds and complement electrostatic properties by conformational search. Based on the binding energy, the molecules are ranked and the top 200 compounds are selected. In addition, molecules similar to the one constructed from de novo ligand design can be identified in the databases using three-dimensionally constrained fragment search. The short listed molecules obtained both by database search (DOCK) and fragment search are used to create a small chemical database library using MDL's project library software. Quantitative Structure Activity Relation (QSAR) analysis in medicinal chemistry and pharmacology has proven useful in making predictions for molecules that are chemically similar to those of the original data set. Distance geometry directed QSAR allows for testing of a much wider class of compounds due to its independence from physico/chemical parameters. The molecules in the library are compared for a common motif and analysis similar to 3D-QSAR are carried out using ASP and TSAR (Oxford Molecular, Oxford, England) sequentially to find the suitable functional groups for maximal binding energy. Finally, compounds selected from different approaches are evaluated using biological activities.

Cytotoxicity Assay

The murine fibroblast cell line, L929 is maintained in Dulbecco's modified Eagle's medium supplemented with 10% FCS, and the medium is replaced with serum free AIM-V medium (GIBCO BRL) right before seeding of the cells for an assay. L929 cells are seeded onto 96-well microtiter plates ($2 \times 10^4$ cells/well), and incubated for 20 hr at 37° C. under 5% $CO_2$ in air. After preincubation with actinomycin D (ACT-D) for 2 hr at a final concentration of 1 mg/ml, TNFα (7 pg)/inhibitor solution (100-80 ml), preincubated in PBS for 1 hr at 37° C., is added to the wells. The cells are incubated with TNFa finally adjusted to 50 pg/ml for 7 hr at 37° C. under 5% $CO_2$, and stained with MTT (Sigma). Briefly, 10 ml of the 10 mg/ml solution of MTT is added to each well, and after 2 hr incubation at 37° C., the formazan formed is colored by overnight incubation at 37° C. with 100 ml of extraction buffer (20% SDS in 50% DMF, pH 4.7). Finally the optical density of colored formazan is measured at 600 nm.

Competitive Radioreceptor Assay

TNF-receptor chimeric protein (100 ng/ml) diluted in PBS (100 ml) is immobilized onto MicroTest III flexible assay plate (Becton Dickinson, San Jose, Calif.) by an incubation at 4° C. overnight. After blocking with PBS containing 1% bovine serum albumin (BSA) for 2 hr at room temperature and subsequent washing with PBS containing 0.1% Tween 20 (PBS-Tw), $^{125}$I-labeled-TNFα (1 ng)/inhibitor solution (100 ml) preincubated in PBS for 1 hr at 37° C. are added onto the TNF-receptor coated wells. After 2 hr incubation at 37° C., the plate is washed with PBS-Tw, and bound radioactivity is measured in Cobra gamma counter (Packard Instruments, Meriden, Conn.).

In some embodiments, the pharmaceutical compositions of the present invention comprise compounds having Formula I which is set forth in the section below entitled Formulae. In compound of Formula I, $R_1$ and $R_2$ are, independently, selected from the group consisting of —H, —$OCH_3$, —$CH_2CH_3$, -t-butyl, 3-carboxy-4-chlorophenylamino, —N—$(CH_2CH_2OH)_2$, and —O(O)C-Ph. $R_3$ is selected from the group consisting of —H, ethyl, —$OCH_3$, —Cl, Br, F, 3-carboxy-4-chlorophenylamino, —N—$(CH_2CH_2OH)_2$, -t-butyl, and —OC(O)-Ph, and is not limited to attachment at any certain position on the phenyl ring to which it is attached. Preferably, $R_3$ is attached at either the 1 or 4 position of the phenyl ring. $R_4$ is selected from the group consisting of —Br, —Cl, and —F.

In some preferred compounds of Formula I
  $R_1, R_2$, and $R_3$ are —$OCH_3$, $R_3$ is attached at the 4 position, $R_4$ is —Cl;
  $R_1$ and $R_2$ are methyl, $R_3$ is ethyl, attached at the 4 position, $R_4$ is —Cl;
  $R_1$ and $R_2$ are —$OCH_3$, $R_3$ is —Cl, attached at the 2 position, $R_4$ is —Cl;
  $R_1$ and $R_2$ are —$OCH_3$ and $R_3$ is H, $R_4$ is —Cl;
  $R_1$ is H, $R_2$ and $R_3$ are 3-carboxy-4-chlorophenylamino, and $R_3$ is attached at the 4 position, $R_4$ is —Cl;
  $R_1$ and $R_2$ are —$N(CH_2CH_2OH)_2$, $R_3$ is Cl, attached at the 4 position, $R_4$ is —Cl;
  $R_1, R_2$, and $R_3$ are t-butyl, $R_3$ is attached at the 4 position, $R_4$ is —Cl;
  $R_1$ is —$OCH_3$, $R_2$ and $R_3$ are H, $R_4$ is Cl; or
  $R_1, R_2$, and $R_3$ are benzoate, $R_3$ is attached at the 4 position, $R_4$ is —Br.

Some preferred compounds of Formula I have the structures I-A, I-B, I-C, I-D, I-E, I-F, I-G, I-H or I-I which are set forth below in the section entitled Formulae.

These compounds are available from the following suppliers:

| Compound | Catalog Number | Supplier |
| --- | --- | --- |
| I-A | F36,700-1 | Aldrich, Milwaukee, WI |
| I-B | S11,245-3 | Aldrich, Milwaukee, WI |
| I-C | 00569 | Ryan Scientific, Isle of Palms, S.C. |
| I-D | F10,001-3 | Aldrich, Milwaukee, WI |
| I-E | 00129 | George UHE, Paramus, NJ |
| I-F | F37,166-1 | Aldrich, Milwaukee, WI |
| I-G | S-11,239-9 | Aldrich, Milwaukee, WI |
| I-H | F-27,721-5 | Aldrich, Milwaukee, WI |
| I-I | F12,920-8 | Aldrich, Milwaukee, WI |

In some embodiments, the pharmaceutical compositions of the present invention comprise compounds having Formula II which is set forth below in the section entitled Formulae. In compounds having Formula II, $R_1$ is selected from the group consisting of -diphenylchloro methyl, -di(4-chlorophenyl)chloro methyl, and 4-(diphenylchloromethyl)phenyl; and $R_2$, $R_3$, $R_4$ are independently selected from the group consisting of —Br, —Cl, and —F, and are preferably —Cl.

Preferred compounds of Formula II have the structures II-A, II-B, II-C and II-D which are set forth below in the section entitled Formulae. These compounds are available from the following suppliers:

| Compound | Catalog Number | Supplier |
| --- | --- | --- |
| II-A | S5,479-9 | Aldrich, Milwaukee, WI |
| II-B | S5,755-0 | Aldrich, Milwaukee, WI |
| II-C | S5,740-2 | Aldrich, Milwaukee, WI |
| II-D | S5,751-8 | Aldrich, Milwaukee, WI |

In some embodiments, the pharmaceutical compositions of the present invention comprise compounds having Formula III which is set forth in the section below entitled Formulae. In compound of Formula III, $R_1$ is H or diethylamino; $R_2$ is —O— or —N($C_6H_6$)—, and $R_3$ is —Br, Cl, or F.

Preferred compounds of Formula III have the structure III-A and III-B which are set forth below in the section entitled Formulae.

These compounds are available from the following suppliers:

| Compound | Catalog Number | Supplier |
| --- | --- | --- |
| III-A | F21,855-5 | Aldrich, Milwaukee, WI |
| III-B | C-390 | Biosynth, Naperville, IL |

Example 2

Pharmaceutical compositions are prepared using compounds of Formulas I, II and III which are commercially available from chemical suppliers such as Sigma, Aldrich, ICN, Ryan Scientific, George Uhe (Paramus, N.J.), and Biosynth (Naperville, Ill.). The pharmaceutical compositions are useful to treat individuals suffering from TNF-mediated diseases, disorders and conditions. Examples of TNF-mediated diseases, disorders and conditions include, for example, inflammatory diseases and autoimmune diseases such as rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease, ulcerative colitis, Lupus (SLE), Grave's disease, myasthenia gravis, autoimmune hemolytic anemia, autoimmune thrombocytopenia, asthma, cryoglobulinemic, primary biliary sclerosis and pernicious anemia. According to the present invention, individuals suffering from such diseases, disorders and conditions may be treated by administering to them a therapeutically effective amount of a pharmaceutical composition that comprises a compound having Formula I, II and III.

The method may include administration of compounds to mammals, preferably humans, in therapeutically effective amounts which are effective to inhibit TNF-mediated diseases. The dosage administered in any particular instance will depend upon factors such as the pharmacodynamic characteristics of the compound, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 µg to about 10 grams per day. In some preferred embodiments, the daily dosage compound will be in the range of from about 10 mg to about 1 gram per day. In some preferred embodiments, the daily dosage compound will be in the range of from about 100 mg to about 500 mg per day. It is contemplated that the daily dosage of a compound used in the method that is the invention will be in the range of from about 1 µg to about 100 mg per kg of body weight, in some embodiments, from about 1 µg to about 40 mg per kg body weight; in some embodiments from about 10 µg to about 20 mg per kg per day, and in some embodiments 10 µg to about 1 mg per kg per day.

Pharmaceutical compositions may be administered in a single dosage, divided dosages or in sustained release. In some preferred embodiments, the compound will be administered in multiple doses per day. In some preferred embodiments, the compound will be administered in 3-4 doses per day.

Persons of ordinary skill will be able to determine dosage forms and amounts with only routine experimentation based upon the considerations of this invention.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See *Remington's Pharmaceutical Sciences*, $18^{th}$ Edition, A. R. Gennaro, Ed., Mack Publishing Company, Easton, Pa., which is incorporated herein by reference.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorobutanol.

Example 3

In one embodiment of the invention, CIAM technology is used to identify compounds that inhibit interactions between CD4, and MHC/antigen/TCR complexes.

By inhibiting CD4, the T cell activation associated with MHC/antigen/TCR complexes can be reduced and immune responses suppressed accordingly. The crystal structure of the CD4 complex shows distinct binding sites.

Peptidomimetics were developed and tested from surface loops of CD4. A peptidomimetic engineered from a CD4 domain inhibited T cell activation associated with MHC/antigen/TCR complexes.

Using the location of the functionally active amino acid sequence identified using the peptidomimetic as the location of a functionally critical active site, the surface of the CD4 molecule was reviewed and a large cleft was identified that could be utilized for docking a pseudo-allosteric inhibitor. The interior of the cavity was mapped and a chemical database was searched. A compound with binding energy of −34 Kcal/mol and having Formula IV was identified. This compound which is commercially available from Salor/Aldrich (Catalog #S69, 246-8) showed activity in in vitro T cell activation assays.

Pharmaceutical compositions are prepared using the compound of Formula IV, V or VI which are set forth in the section below entitled Formulae. The pharmaceutical compositions are useful to treat individuals suffering from CD4-mediated diseases, disorders and conditions. Examples of CD4-mediated diseases, disorders and conditions include, for example, inflammatory diseases and autoimmune diseases such as rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease, ulcerative colitis, Lupus (SLE), Grave's disease, myasthenia gravis, autoimmune hemolytic anemia, autoimmune thrombocytopenia, asthma, cryoglobulinemic, primary biliary sclerosis and pernicious anemia. According to the present invention, individuals suffering from such diseases, disorders and conditions may be treated by administering to them a therapeutically effective amount of a pharmaceutical composition that comprises a compound having either Formula IV, V or VI.

The method may include administration of compounds to mammals, preferably humans, in therapeutically effective amounts which are effective to inhibit CD4-mediated diseases. The dosage administered in any particular instance will depend upon factors such as the pharmacodynamic characteristics of the compound, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 µg to about 10 grams per day. In some preferred embodiments, the daily dosage compound will be in the range of from about 10 mg to about 1 gram per day. In some preferred embodiments, the daily dosage compound will be in the range of from about 100 mg to about 500 mg per day. It is contemplated that the daily dosage of a compound used in the method that is the invention will be in the range of from about 1 µg to about 100 mg per kg of body weight, in some embodiments, from about 1 µg to about 40 mg per kg body weight; in some embodiments from about 10 µg to about 20 mg per kg per day, and in some embodiments 10 µg to about 1 mg per kg per day.

Pharmaceutical compositions may be administered in a single dosage, divided dosages or in sustained release. In some preferred embodiments, the compound will be administered in multiple doses per day. In some preferred embodiments, the compound will be administered in 3-4 doses per day.

Persons of ordinary skill will be able to determine dosage forms and amounts with only routine experimentation based upon the considerations of this invention.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See *Remington's Pharmaceutical Sciences*, 18th Edition, A. R. Gennaro, Ed., Mack Publishing Company, Easton, Pa., which is incorporated herein by reference.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorobutanol.

Example 4

In one embodiment of the invention, CIAM technology is used to identify compounds that inhibit β-lactamase. Inhibition of the enzyme β-lactamase is useful to render penicillin-resistant strains of bacteria, penicillin-sensitive. A cavity with the criteria described above proximal from the active site of β-lactamase was identified by β-factors and thermodynamic analysis.

The surface of the β-lactamase molecule was reviewed and a proximal suitable cleft was identified that could be utilized for docking an allosteric inhibitor. The cavity was mapped and a chemical database was searched. A series of compounds were identified. These compounds are shown as Formulae VII-XIX in the section below entitled Formulae. They are commercially available from several suppliers including Aldrich (Milwaukee, Wis., Sigma, Fluka, ICN, Ryan Scientific (Isle of Palms, S.C.), SynTec (Germany) and Bayer (Leverkusen, Germany).

Pharmaceutical compositions are prepared using one of the compounds selected from the group of Formula VII-XIX. The pharmaceutical compositions are useful to treat individuals suffering from bacterial infectious, particularly those which are penicillin resistant. According to the present invention, individuals suffering from such infections may be treated by administering to them a therapeutically effective amount of a pharmaceutical composition that comprises a compound having Formula VII, VIII, IX, X, XI, XII, XIII, XIV, XV, XVI, XVII, XVIII or XIX in combination with penicillin-derived antibiotic.

The method may include administration of compounds to mammals, preferably humans, in therapeutically effective amounts which are effective to inhibit β-lactamase in order to render penicillin-resistant strains of bacteria penicillin-sensitive. The dosage administered in any particular instance will depend upon factors such as the pharmacodynamic characteristics of the compound, its mode and route of administration; age, health, and weight of the recipient; nature and extent of symptoms; kind of concurrent treatment, frequency of treatment, and the effect desired.

It is contemplated that the daily dosage of the compound used in the method that is the invention will be in the range of from about 1 µg to about 10 grams per day. In some preferred embodiments, the daily dosage compound will be in the range of from about 10 mg to about 1 gram per day. In some preferred embodiments, the daily dosage compound will be in the range of from about 100 mg to about 500 mg per day. It is contemplated that the daily dosage of a compound used in the method that is the invention will be in the range of from about 1 µg to about 100 mg per kg of body weight, in some embodiments, from about 1 μg to about 40 mg per kg body weight; in some embodiments from about 10 μg to about 20 mg per kg per day, and in some embodiments 10 μg to about 1 mg per kg per day.

Pharmaceutical compositions may be administered in a single dosage, divided dosages or in sustained release. In some preferred embodiments, the compound will be administered in multiple doses per day. In some preferred embodiments, the compound will be administered in 3-4 doses per day.

Persons of ordinary skill will be able to determine dosage forms and amounts with only routine experimentation based upon the considerations of this invention.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See *Remington's Pharmaceutical Sciences*, 18$^{th}$ Edition, A. R. Gennaro, Ed., Mack Publishing Company, Easton, Pa., which is incorporated herein by reference.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfate, sodium sulfite, and ascorbic acid, citric acid and its salts, and sodium EDTA. Suitable preservatives include benzalkonium chloride, methyl- or propyl-paraben, and chlorobutanol.

In some embodiments, the pharmaceutical compositions of the present invention used in the methods of the present invention comprise compounds having Formulae VII-XVI.

In some embodiments, the pharmaceutical compositions of the present invention comprise compounds having Formula VII.

In some embodiments, the pharmaceutical compositions of the present invention comprise compounds having Formula VIII.

Compounds according to Formula VIII may have at position $R_1$, a group having Formula 8-1-1, 8-1-2, 8-1-3, 8-1-4, 8-1-5, 8-1-6, 8-1-7, 8-1-8, 8-1-9 and 8-1-10 which are set forth below in the section entitled Formulae.

Compounds according to Formula VIII may have at position $R_2$ and $R_2$ are, independently, —H, —$C_1$, —$C_2$, —$C_3$ straight or branched, —$C_4$ straight or branched, —$C_5$ straight or branched, $C_6$ straight or branched, —$C_7$ straight or branched, and —$C_8$ straight or branched. $R_2$ and $R_2$ are preferably identical to each other. $R_2$ and $R_2$ are preferably —H or the —$C_8$ branched 4-tert-octyl.

Some preferred compounds of Formula VIII include compounds wherein:
$R_1$ is 8-1-1, $R_2$ is —H, and $R_3$ is —H;
$R_1$ is 8-1-1, $R_2$ is 4-tert-octyl, and $R_3$ is 4-tert-octyl;
$R_1$ is 8-1-2, $R_2$ is —H and $R_3$ is —H;
$R_1$ is 8-1-3, $R_2$ is —H and $R_3$ is —H;
$R_1$ is 8-1-4, $R_2$ is —H and $R_3$ is —H;
$R_1$ is 8-1-5, $R_2$ is —H and $R_3$ is —H;
$R_1$ is 8-1-6, $R_2$ is —H and $R_3$ is —H;
$R_1$ is 8-1-7, $R_2$ is —H and $R_3$ is —H;
$R_1$ is 8-1-8, $R_2$ is —H and $R_3$ is —H;
$R_1$ is 8-1-9, $R_2$ is —H and $R_3$ is —H; and
$R_1$ is 8-1-10, $R_2$ is —H and $R_3$ is —H.

Some preferred compounds of Formula VIII include structure VIII-A, VIII-B, VIII-C, VIII-D, VIII-E, VIII-F, VIII-G, VIII-H, VIII-I, VIII-J or which are set forth below in the section entitled Formulae.

| Compund | Source | Catalog Number |
|---|---|---|
| VIII-A. | ALDRICH | F28,168-9 |
| VIII-B. | ALDRICH | 25,762-1 |
| VIII-C. | SIGMA-ALDRICH | S68,073-7 |
| VIII-D. | SIGMA-ALDRICH | S15,490-3 |
| VIII-E. | SIGMA-ALDRICH | S15,495-4 |
| VIII-F. | SIGMA-ALDRICH | S15,498-9 |
| VIII-G. | SIGMA-ALDRICH | S15,504-0 |
| VIII-H. | SIGMA-ALDRICH | S15,505-5 |
| VIII-I. | SIGMA-ALDRICH | R17,712-1 |
| VIII-J. | SIGMA-ALDRICH | R17,271-5 |
| VIII-K. | SIGMA-ALDRICH | R17,703-2 |

In some embodiments, the pharmaceutical compositions of the present invention comprise compounds having Formula IX.

Compounds according to Formula IX may have at position $R_1$, $R_2$, $R_3$ and $R_4$, independently, —H, —$OC_6H_5Cl$, —$N(CH_3)_2$, —$OCH_3$, —$CH_3$, —OH or -halogen, and if halogen, preferably —Cl. In some preferred embodiments, $R_1$ is —$OCH_3$, —OH or -halogen, and if halogen, preferably —Cl. In some preferred embodiments $R_2$ is —H, —$N(CH_3)_2$, —$OCH_3$, —$CH_3$, or -halogen, and if halogen, preferably —Cl. In some preferred embodiments $R_3$ is —$OCH_3$, —$CH_3$, —OH or -halogen, and if halogen, preferably —Cl. In some preferred embodiments $R_4$ is —$OC_6H_5Cl$, —$OCH_3$, —$CH_3$ or —OH.

Some preferred compounds of Formula IX include compounds wherein:
$R_1$ is —Cl, $R_2$ is —H, $R_3$ is —Cl and $R_4$ is $OC_6H_5Cl$;
$R_1$ is —$N(CH_3)_2$, $R_2$ is —H, $R_3$ is —Cl and $R_4$ is —$OCH_3$;
$R_1$ is —$OCH_3$, $R_2$ is —H, $R_3$ is —$OCH_3$ and $R_4$ is —$OCH_3$;
$R_1$ is —Cl, $R_2$ is —H, $R_3$ is —Cl and $R_4$ is —$OCH_3$;
$R_1$ is —Cl, $R_2$ is —H, $R_3$ is —$CH_3$ and $R_4$ is —$OCH_3$;
$R_1$ is —$OCH_3$, $R_2$ is —Cl, $R_3$ is —H and $R_4$ is —OH;
$R_1$ is —OH, $R_2$ is —H, $R_3$ is —Cl and $R_4$ is —$OCH_3$;
$R_1$ is —$OCH_3$, $R_2$ is —H, $R_3$ is —$CH_3$ and $R_4$ is —$OCH_3$;
$R_1$ is —Cl, $R_2$ is —Cl, $R_3$ is —$OCH_3$ and $R_4$ is —$OCH_3$;
$R_1$ is —Cl, $R_2$ is —H, $R_3$ is —$OCH_3$ and $R_4$ is —$OCH_3$;
$R_1$ is —$OCH_3$, $R_2$ is —H, $R_3$ is —$OCH_3$ and $R_4$ is —$OCH_3$;
$R_1$ is —$OCH_3$, $R_2$ is —$CH_3$, $R_3$ is —Cl and $R_4$ is —H;
$R_1$ is —OH, $R_2$ is —H, $R_3$ is —Cl and $R_4$ is —$CH_3$; and
$R_1$ is —$OCH_3$, $R_2$ is —$OCH_3$, $R_3$ is —OH and $R_4$ is —H.

Some preferred compounds of Formula IX include structure IX-A, IX-B, IX-C, IX-D, IX-E, IX-F, IX-G, IX-H, IX-I, IX-J, IX-K, IX-L, LX-M or IX-N which are set forth below in the section entitled Formulae.

| Compund | Source | Catalog Number |
|---|---|---|
| IX-A. | SIGMA-ALDRICH | S50,872-1 |
| IX-B. | SIGMA-ALDRICH | S69,044-9 |
| IX-C. | SIGMA-ALDRICH | S69,613-7 |
| IX-D. | SIGMA-ALDRICH | S69-516-5 |
| IX-E. | SIGMA-ALDRICH | S12,931-3 |
| IX-F. | SIGMA-ALDRICH | S72,315-0 |
| IX-G. | SIGMA-ALDRICH | S69,055-4 |
| IX-H. | SIGMA-ALDRICH | S76,872-3 |
| IX-I. | SIGMA-ALDRICH | S90,369-8 |
| IX-J. | SIGMA-ALDRICH | S90,370-1 |
| IX-K. | SIGMA-ALDRICH | S74,299-6 |
| IX-L. | SIGMA-ALDRICH | S72,956-6 |
| IX-M. | SIGMA-ALDRICH | S91,728-1 |
| IX-N. | SIGMA-ALDRICH | S91,730-3 |

In some embodiments, the pharmaceutical compositions of the present invention comprise compounds having Formula X.

Compounds according to Formula X may have at position $R_1$ a group having Formula 10-1-1, 10-1-2 or 10-1-3 which are set forth below in the section entitled Formulae.

Compounds according to Formula X may have at position $R_2$, $R_3$ and $R_4$ are, independently, —H, —$NO_2$, —$NH_2$ or —$CH_3$. $R_2$ is preferably —H or —$NH_2$. $R_3$ is preferably —$NO_2$ or —$NH_2$. $R_4$ is preferably —H or —$CH_3$.

Some preferred compounds of Formula X include compounds wherein:
$R_1$ is 10-1-1, $R_2$ is —H, $R_3$ is —$NO_2$ and $R_4$ is —H;
$R_1$ is 10-1-2, $R_2$ is —H, $R_3$ is —$NO_2$ and $R_4$ is —H; and
$R_1$ is 10-1-3, $R_2$ is —$NH_2$, $R_3$ is —$NH_2$ and $R_4$ is —$CH_3$.

Some preferred compounds of Formula X include structure X-A, X-B or X-C which are set forth below in the section entitled Formulae.

| Compound | Source | Catalog Number |
|---|---|---|
| X-A. | RYAN SCIENTIFIC | NRB01150 |
| X-B. | SIGMA | S93,056-3 |
| X-C. | ALDRICH | 21,222-9 |

In some embodiments, the pharmaceutical compositions of the present invention comprise compounds having Formula XI.

Compounds according to Formula XI may have at position $R_1$ and $R_2$, independently, a group having Formula 11-1/2-1, 11-1/2-2, 11-1/2-3, 11-1/2-4, which are set forth below in the section entitled Formulae, or —H, —$NO_2$ or —OH Compounds according to Formula XI may have at position $R_3$ either —H, —$NH_2$, —OH, or halogen, and when $R_3$ is halogen, it is preferably —Cl or —Br.

Compounds according to Formula XI may have at position $R_3$ either —H, —$NH_2$, —OH, or halogen, and when $R_3$ is halogen, it is preferably —Cl or —Br.

Compounds according to Formula XI may have at position $R_4$ either —H or —$CH(CH_3)_3$.

Some preferred compounds of Formula XI include compounds wherein:
$R_1$ is 11-1/2-1, $R_2$ is 11-1/2-1, $R_3$ is —H and $R_4$ is —H;
$R_1$ is 11-1/2-2, $R_2$ is 11-1/2-2, $R_3$ is —$NH_2$ and $R_4$ is —H;
$R_1$ is 11-1/2-3, $R_2$ is 11-1/2-3, $R_3$ is —Cl and $R_4$ is —H;
$R_1$ is 11-1/2-4, $R_2$ is —H, $R_3$ is —$NO_2$ and $R_4$ is —H; and
$R_1$ is —$NO_2$, $R_2$ is —OH, $R_3$ is —OH and $R_4$ is —H.

Some preferred compounds of Formula XI include structure XI-A, XI-B, XI-C, XI-D or XI-E which are set forth below in the section entitled Formulae.

| Compound | Source | Catalog Number |
|---|---|---|
| XI-A. | SIGMA-ALDRICH | S18,982-0 |
| XI-B. | SIGMA-ALDRICH | S18,611-2 |
| XI-C. | SIGMA | S3,634-0 |
| XI-D. | SIGMA | S86,927-9 |
| XI-E. | SIGMA | S53,622-9 |

In some embodiments, the pharmaceutical compositions of the present invention comprise compounds having Formula XII.

Compounds according to Formula XII may have at position $R_1$ either N-pyridinium, 4-methyl-N-pyridinium, 4-dimethylamino-N-pyridinium, 3-methyl-N-pyridinium, N-pyridinium, 2,6 dimethyl-N-pyridinium, 3,5 dimethyl-N-pyridinium, 3-ethyl-N-pyridinium, 12-1-1, 12-1-2 which are set forth below in the section entitled Formulae, or 4-ethyl-N-pyridinium, 4-benzyl-N-pyridinium, N-quinolinyl or $CH_3$.

Some preferred compounds of Formula XII include compounds wherein:
$R_1$ is N-pyridinium and $R_2$ is $NO_2$;
$R_1$ is 4-methyl-N-pyridinium and $R_2$ is $NO_2$;
$R_1$ is 4-dimethylamino-N-pyridinium and $R_2$ is $NO_2$;
$R_1$ is 3-methyl-N-pyridinium and $R_2$ is $NO_2$;
$R_1$ is N-pyridinium and $R_2$ is $NO_2$;
$R_1$ is 2,6 dimethyl-N-pyridinium and $R_2$ is $NO_2$;
$R_1$ is 3,5 dimethyl-N-pyridinium and $R_2$ is $NO_2$;
$R_1$ is 3-ethyl-N-pyridinium and $R_2$ is $NO_2$;
$R_1$ is 12-1-1 and $R_2$ is $NO_2$;
$R_1$ is 12-1-2 and $R_2$ is $NO_2$;
$R_1$ is 4-ethyl-N-pyridinium and $R_2$ is $NO_2$;
$R_1$ is 4-benzyl-N-pyridinium and $R_2$ is $NO_2$;
$R_1$ is N-quinolinyl and $R_2$ is $NO_2$; and
$R_1$ is $CH_3$ and $R_2$ is H.

Some preferred compounds of Formula XII include structure XII-A, XII-B, XII-C, XII-D, XII-E, XII-F, XII-G, XII-H, XII-I, XII-J, XII-K, XII-L, XII-M or XII-N, which are set forth below in the section entitled Formulae.

| Compound | Source | Catalog Number |
|---|---|---|
| XII-A. | SIGMA | S14,318-9 |
| XII-B. | SIGMA | S96,676-2 |
| XII-C. | SIGMA | S14,440-1 |
| XII-D. | SIGMA | S96,664-9 |
| XII-E. | SIGMA | S96,668-1 |
| XII-F. | SIGMA | S96,670-3 |
| XII.G. | SIGMA | S14,386-3 |
| XII-H. | SIGMA | S96,674-6 |
| XII-I. | SIGMA | S96,682-7 |
| XII-J. | SIGMA | S96,677-0 |
| XII-K. | SIGMA | S96,679-7 |
| XII-L. | SIGMA | S96,685-1 |
| XII-M. | SIGMA | S14,675-7 |
| XII-N. | SIGMA-ALDRICH | S67,954-2 |

In some embodiments, the pharmaceutical compositions of the present invention comprise compounds having Formula XIII which is set forth in the section below entitled Formulae. Compounds having Formula XIII are available from SIGMA-ALDRICH, Catalog number S42,591-5.

In some embodiments, the pharmaceutical compositions of the present invention comprise compounds having Formula XIV.

Compounds according to Formula XIV may have at position $R_1$ either —$OCH_3$, —$NO_2$ or -halogen, and if -halogen, preferably —Cl.

Compounds according to Formula XIV may have at position $R_2$ either —H, —$NO_2$ or -halogen, and if -halogen, preferably —Cl.

Some preferred compounds of Formula XIV include compounds wherein:

$R_1$ is —Cl and $R_2$ is —Cl;
$R_1$ is —$OCH_3$ and $R_2$ is —H;
$R_1$ is —Cl and $R_2$ is —H; and
$R_1$ is —$NO_2$ and $R_2$ is $NO_2$.

Some preferred compounds of Formula XIV include structure XIV-A, XIV-B, XIV-C or XIV-D which are set forth in the section below entitled Formulae.

| Compound | Source | Catalog Number |
|---|---|---|
| XIV-A. | SIGMA | S6,886-2 |
| XIV-B. | SIGMA | S12,703-5 |
| XIV-C. | SIGMA | S62,321-0 |
| XIV-D. | SIGMA | S24,232-2 |

In some embodiments, the pharmaceutical compositions of the present invention comprise compounds having Formula XV.

Compounds according to Formula XV may have at position $R_1$ either —H, —$NO_2$, —$FSO_2$, —$CH_3$, —$OCH_3$, —$SO_2CH_3$, 15-1-1, 15-1-2 or 15-1-3 which are set forth in the section below entitled Formulae.

Compounds according to Formula XV may have at position $R_2$ either —H, —OH, or —$NO_2$.

Compounds according to Formula XV may have at position $R_3$ either —H or —OH.

Compounds according to Formula XV may have at position $R_4$ either —H, 15-4-1, 15-4-2, 15-4-3, 15-4-4, 15-4-5, 15-4-6, 15-4-7, 15-4-8, 15-4-9, 15-4-10, 15-4-11, 15-4-12 which are set forth in the section below entitled Formulae or halogen, and when $R_4$ is halogen, it is preferably —Cl.

Some preferred compounds of Formula XV include compounds wherein:

$R_1$ is —$NO_2$, $R_2$ is —H, $R_3$ is —OH and $R_4$ is —Cl;
$R_1$ is —H, $R_2$ is —OH, $R_3$ is —H and $R_4$ is -15-4-1;
$R_1$ is —$FSO_2$, $R_2$ is —$NO_2$, $R_3$ is —OH and $R_4$ is —H;
$R_1$ is 15-1-1, $R_2$ is —$NO_2$, $R_3$ is —OH and $R_4$ is —H;
$R_1$ is —H, $R_2$ is —H, $R_3$ is —H and $R_4$ is 15-4-2;
$R_1$ is —H, $R_2$ is —H, $R_3$ is —OH and $R_4$ is 15-4-3;
$R_1$ is —H, $R_2$ is —H, $R_3$ is —OH and $R_4$ is 15-4-5;
$R_1$ is —H, $R_2$ is —OH, $R_3$ is —$OCH_3$ and $R_4$ is 15-4-6;
$R_1$ is —$OCH_3$, $R_2$ is —H, $R_3$ is —OH and $R_4$ is 15-4-7;
$R_1$ is —H, $R_2$ is —H, $R_3$ is —OH and $R_4$ is 15-4-8;
$R_1$ is —H, $R_2$ is —H, $R_3$ is —OH and $R_4$ is 15-4-9;
$R_1$ is —$OCH_3$, $R_2$ is —H, $R_3$ is —H and $R_4$ is 15-4-10;
$R_1$ is —$FSO_2$, $R_2$ is —H, $R_3$ is —OH and $R_4$ is 15-4-11;
$R_1$ is —H, $R_2$ is —H, $R_3$ is —H and $R_4$ is 15-4-12;
$R_1$ is —$SO_2CH_3$, $R_2$ is —H, $R_3$ is —OH and $R_4$ is —H;
$R_1$ is 15-1-2, $R_2$ is —H, $R_3$ is —OH and $R_4$ is —H; and
$R_1$ is 15-1-3, $R_2$ is —$NO_2$, $R_3$ is —OH and $R_4$ is —H.

Some preferred compounds of Formula XV include structure XV-A, XV-B, XV-C, XV-D, XV-E, XV-F, XV-G, XV-H, XV-I, XV-J, XV-K, XV-L, XV-M, XV-N, XV-O, XV-P, XV-Q or XV-R which are set forth in the section below entitled Formulae.

| Compound | Source | Catalog Number |
|---|---|---|
| XV-A. | SIGMA | S72,767-9 |
| XV-B. | SIGMA | S72,772-5 |
| XV-C. | SIGMA | S73,689-9 |
| XV-D. | BAYER CORP. | 25/08 |
| XV-E. | SIGMA | S50,245-6 |
| XV-F. | SIGMA | S65,507-4 |
| XV-G. | SIGMA | S78,072-3 |
| XV-H. | SIGMA | S79,426-0 |
| XV-I. | SIGMA | S79,453-8 |
| XV-J. | SIGMA | S80,012-0 |
| XV-K. | SIGMA | S84,486-1 |
| XV-L. | RYAN | NRB01429 |
| XV-M. | SIGMA | S92,407-5 |
| XV-N. | SIGMA | S72,781-4 |

In some embodiments, the pharmaceutical compositions of the present invention comprise compounds having Formula XVI.

Compounds according to Formula XVI may have at position $R_1$ either —H, —$SO_3$ or halogen, and when $R_4$ is halogen, it is preferably —Cl.

Compounds according to Formula XVI may have at position $R_2$ either —H or —$CH_3$.

Compounds according to Formula XVI may have at position $R_3$ either —H, —$OCH_3$, —$NSO_2$—$NO_2$, 16-3-1 which is set forth below in the section entitled Formulae, or halogen, and when $R_3$ is halogen, it is preferably —Fl.

Compounds according to Formula XVI may have at position $R_4$ either —H, —$OCH_3$, —$SO_3$ or halogen, and when $R_4$ is halogen, it is preferably —Cl.

Compounds according to Formula XVI may have at position $R_5$ either —H, —$NO_2$ or halogen, and when $R_5$ is halogen, it is preferably —Cl.

Compounds according to Formula XVI may have at position $R_6$ either —H, —$C(CH_3)_2$ or phenyl.

Some preferred compounds of Formula XVI include compounds wherein:

$R_1$ is —H, $R_2$ is —$CH_3$, $R_3$ is —$OCH_3$, $R_4$ is —$OCH_3$, $R_5$ is —H and $R_4$ is —H,
$R_1$ is —H, $R_2$ is —$CH_3$, $R_3$ is —$NSO_2$, $R_4$ is —H, $R_5$ is —H and $R_6$ is —H,
$R_1$ is —H, $R_2$ is —$CH_3$, $R_3$ is —$OCH_3$, $R_4$ is —Cl, $R_5$ is —H and $R_6$ is —H,
$R_1$ is —$NSO_3$, $R_2$ is —$CH_3$, $R_3$ is —$OCH_3$, $R_4$ is —$SO_3$, $R_5$ is —$NO_2$ and $R_6$ is —H,
$R_1$ is —H, $R_2$ is —H, $R_3$ is —H, $R_4$ is —H, $R_5$ is —H and $R_6$ is —H,
$R_1$ is —H, $R_2$ is —H, $R_3$ is —Cl, $R_4$ is —Cl, $R_5$ is —H and $R_6$ is —H,
$R_1$ is —H, $R_2$ is —$CH_3$, $R_3$ is —F, $R_4$ is —H, $R_5$ is —H and $R_6$ is —H,
$R_1$ is —H, $R_2$ is —$CH_3$, $R_3$ is -16-3-1, $R_4$ is —H, $R_5$ is —H and $R_6$ is —H,
$R_1$ is —H, $R_2$ is —$CH_3$, $R_3$ is —H, $R_4$ is —H, $R_5$ is —H and $R_6$ is —$C(CH_3)_2$.
$R_1$ is —H, $R_2$ is —$CH_3$, $R_3$ is —$OCH_3$, $R_4$ is —$OCH_3$, $R_5$ is —Cl and $R_6$ is —H,
$R_1$ is —H, $R_2$ is —$CH_3$, $R_3$ is —F, $R_4$ is —H, $R_5$ is —H and $R_6$ is —H,
$R_1$ is —Cl, $R_2$ is —H, $R_3$ is —H, $R_4$ is —H, $R_5$ is —H and $R_6$ is —H,
$R_1$ is —Cl, $R_2$ is —H, $R_3$ is —$OCH_3$, $R_4$ is —H, $R_5$ is —H and $R_6$ is —H, or
$R_1$ is —H, $R_2$ is —$CH_3$, $R_3$ is —H, $R_4$ is —H, $R_5$ is —H and $R_6$ is phenyl.

Some preferred compounds of Formula XVI include structure XVI-A, XVI-B, XVI-C, XVI-D, XVI-E, XVI-F, XVI-G, XVI-H, XVI-I, XVI-J, XVI-K, XVI-L, XVI-M or XVI-N which are set forth below in the section entitled Formulae.

| Compound | Source | Catalog Number |
| --- | --- | --- |
| XVI-A. | SIGMA | S53,065-4 |
| XVI-B. | SYNTEC, GERMANY | ST 58/4 |
| XVI-C. | SIGMA | S62,937-5 |
| XVI-D. | SIGMA | S50,191-3 |
| XVI-E. | SIGMA | S21,210-5 |
| XVI-F. | SIGMA | S21,212-1 |
| XVI-G. | SIGMA | S6,965-6 |
| XVI-H. | SIGMA | S6,971-0 |
| XVI-I. | SIGMA | S7,002-6 |
| XVI-J. | SIGMA | S21,225-3 |
| XVI-K. | SIGMA | S21,234-2 |
| XVI-L. | SIGMA | S21,241-5 |
| XVI-M. | SIGMA | S21,243-1 |
| XVI-N. | SIGMA | S63,263-5 |
| XVI-O. | SIGMA | S21,212-1 |
| XVI-P. | SIGMA | S38,916-1 |
| XVI-Q. | SIGMA | S50,242-0 |
| XVI-R. | SIGMA | S62,979-0 |

In some embodiments, the pharmaceutical compositions of the present invention comprise compounds having Formula XVII (SIGMA S86, 927-9).

In some embodiments, the pharmaceutical compositions of the present invention comprise compounds having Formula XVIII (RYAN SCIENTIFIC E191B)

In some embodiments, the pharmaceutical compositions of the present invention comprise compounds having Formula XIX (SIGMA S12, 962-3).

Formulae

FORMULA I

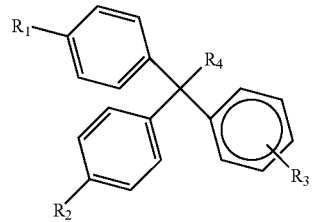

FORMULA II

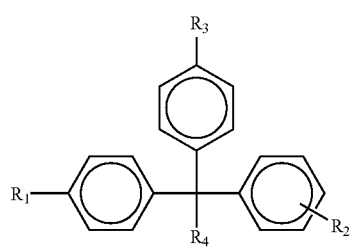

FORMULA II-A

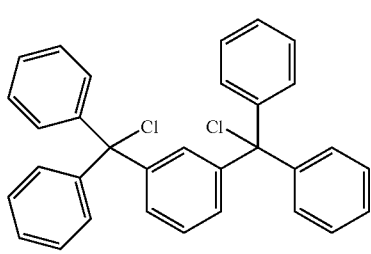

FORMULA II-B

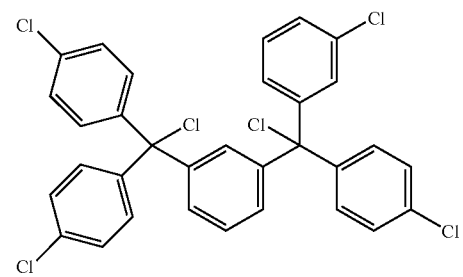

FORMULA II-C

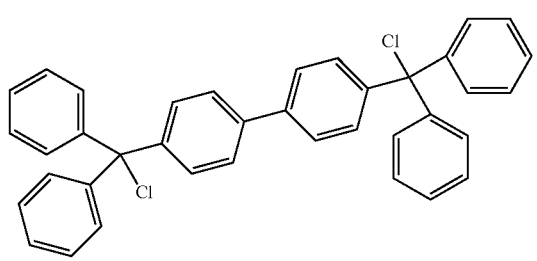

FORMULA II-D

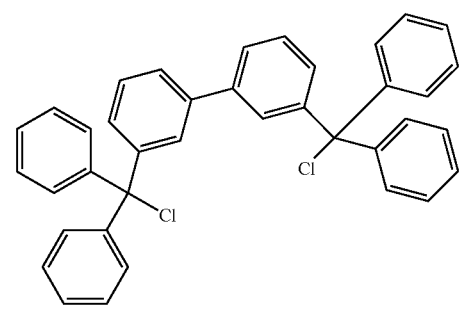

FORMULA III

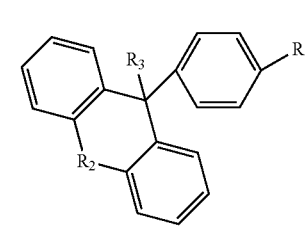

FORMULA III-A

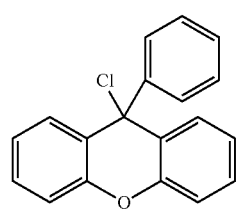

FORMULA III-B
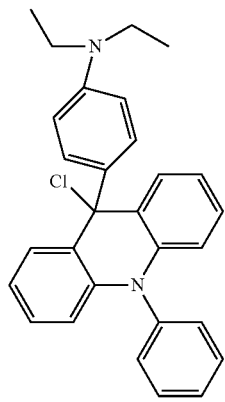
FORMULA IV
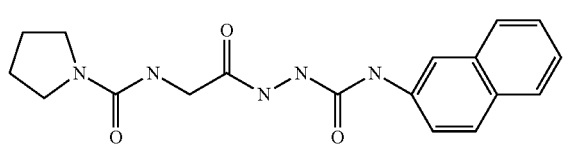
FORMULA V
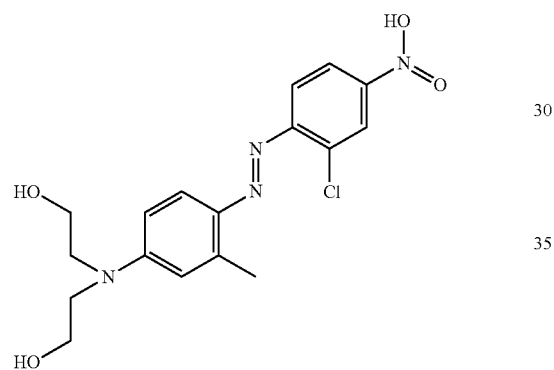
FORMULA VI
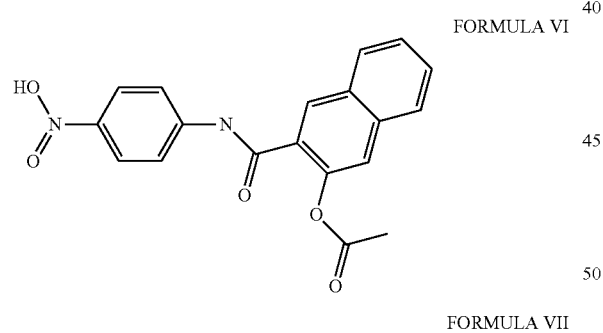
FORMULA VII
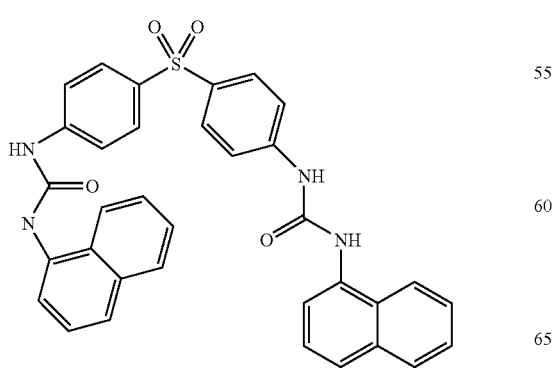
FORMULA VIII
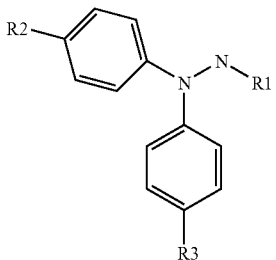
FORMULA 8-1-1
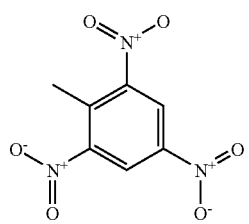
FORMULA 8-1-2
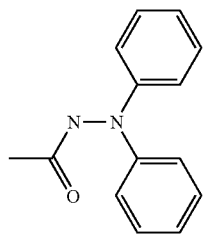
FORMULA 8-1-3
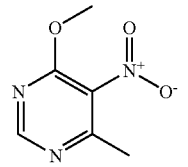
FORMULA 8-1-4
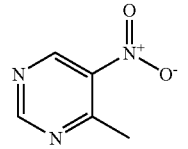
FORMULA 8-1-5
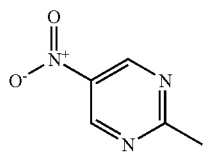
FORMULA 8-1-6
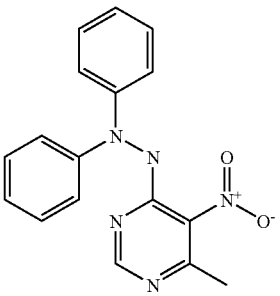

-continued
FORMULA 8-1-7
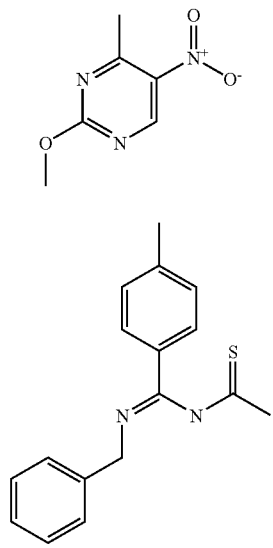
FORMULA 8-1-8
FORMULA 8-1-9
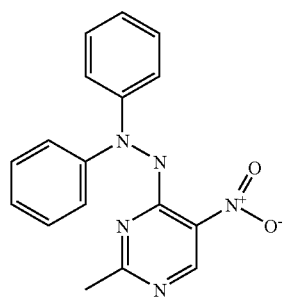
FORMULA 8-1-10
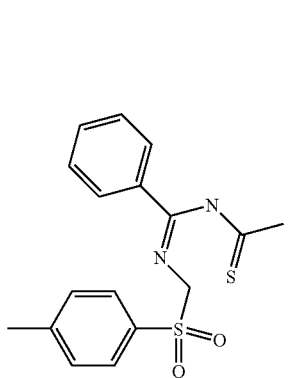
FORMULA 8-A
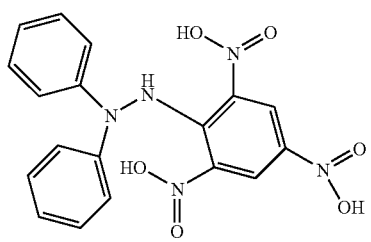
FORMULA 8-B
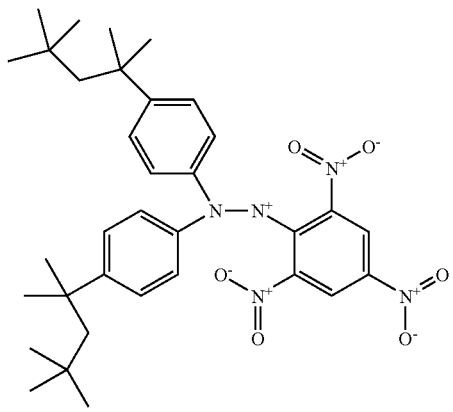
FORMULA 8-C
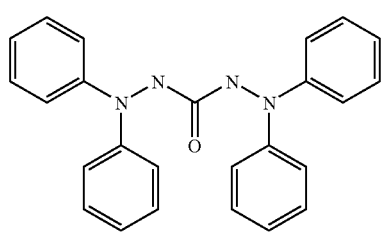
FORMULA 8-D
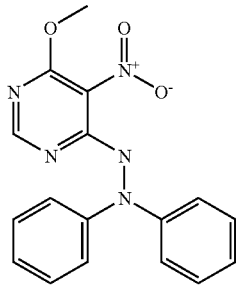
FORMULA 8-E
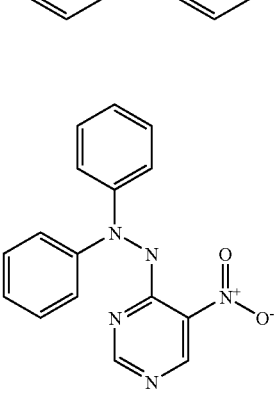
FORMULA 8-F
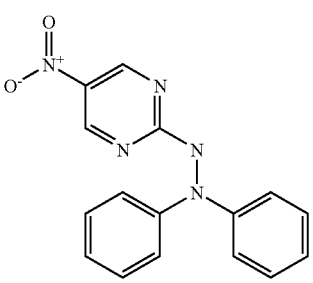

FORMULA 8-G
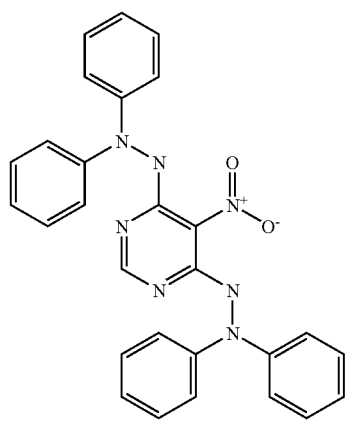
FORMULA 8-H
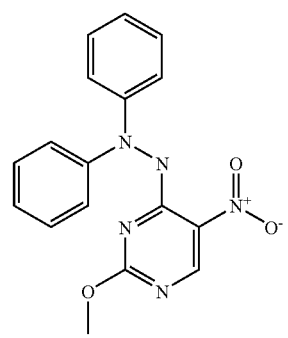
FORMULA 8-I
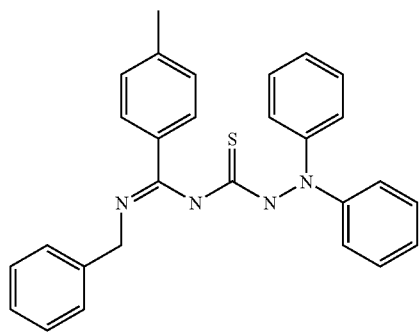
FORMULA 8-J
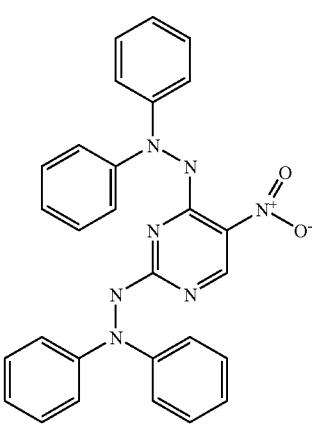
FORMULA 8-K
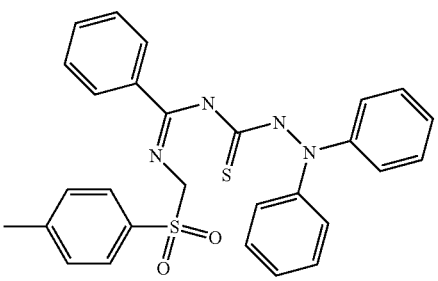
FORMULA IX
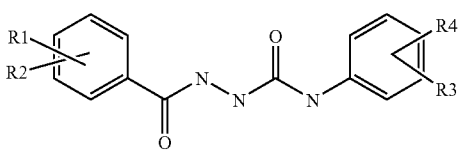
FORMULA IX-A
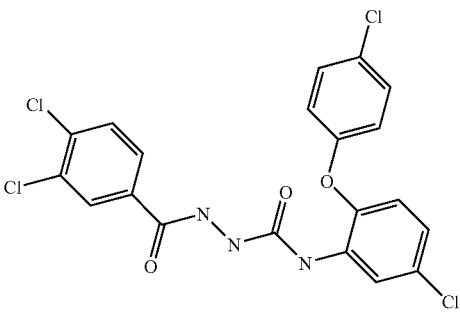
FORMULA IX-B
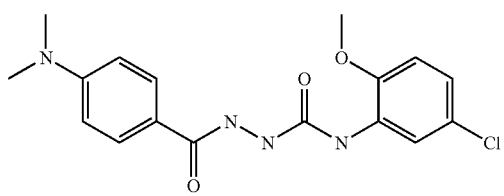
FORMULA IX-C
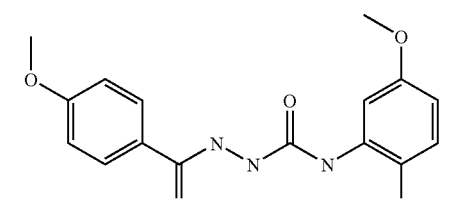
FORMULA IX-D
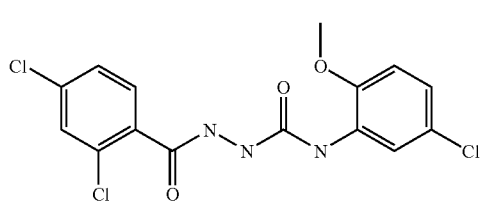

FORMULA IX-E

FORMULA IX-F

FORMULA IX-G

FORMULA IX-H

FORMULA IX-I

FORMULA IX-J

FORMULA IX-K

FORMULA IX-L

FORMULA IX-M

FORMULA IX-N

FORMULA X

FORMULA 10-1-1

FORMULA 10-1-2

FORMULA 10-1-3

FORMULA X-A
FORMULA X-B
FORMULA X-C
FORMULA XI
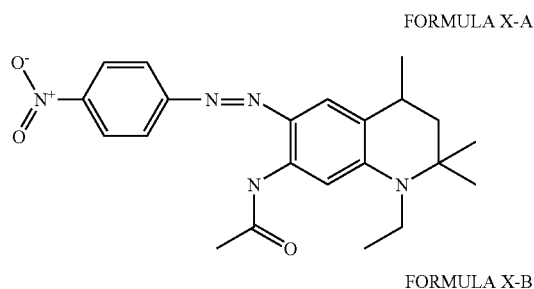
FORMULA 11-1/2-1
FORMULA 11-1/2-2
FORMULA 11-1/2-3
FORMULA 11-1/2-4
FORMULA XI-A
FORMULA XI-B
FORMULA XI-C FORMULA XI-D
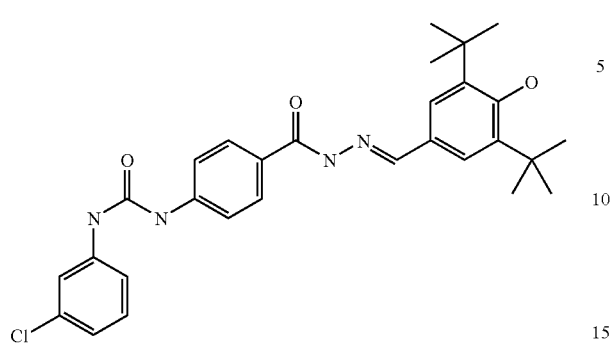
FORMULA XI-E
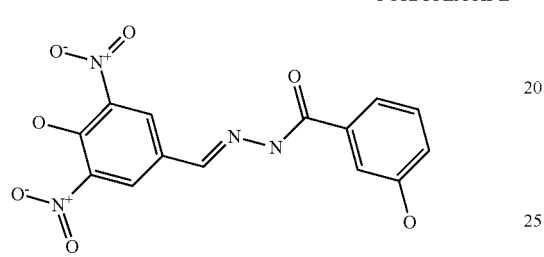
FORMULA XII
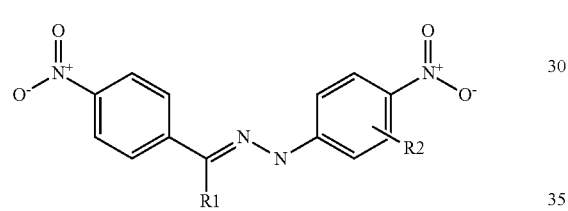
FORMULA 12-1-1
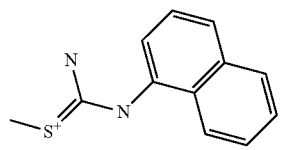
FORMULA 12-1-2
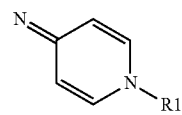
FORMULA XII-A
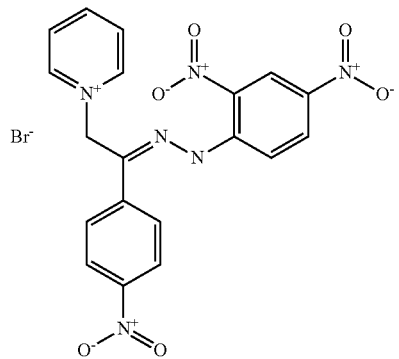
FORMULA XII-B
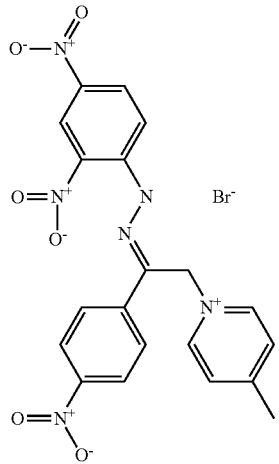
FORMULA XII-C
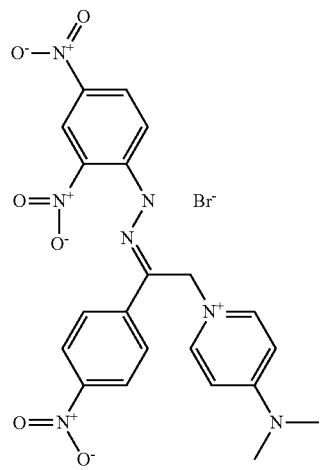
FORMULA XII-D
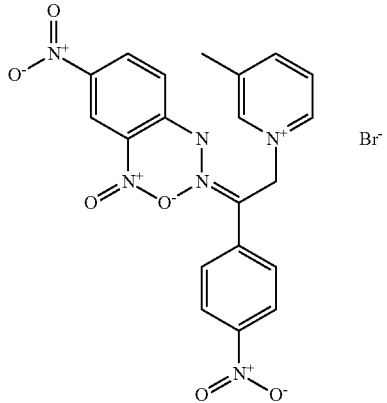

FORMULA XII-E
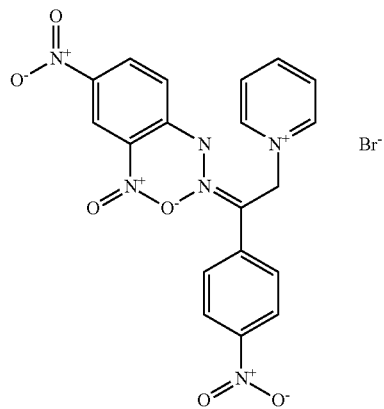
FORMULA XII-F
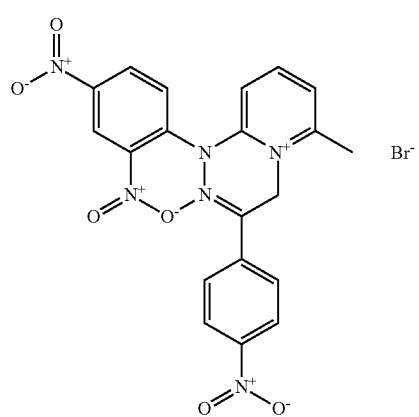
FORMULA XII-G
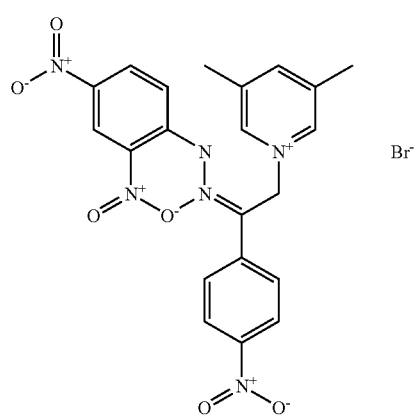
FORMULA XII-H
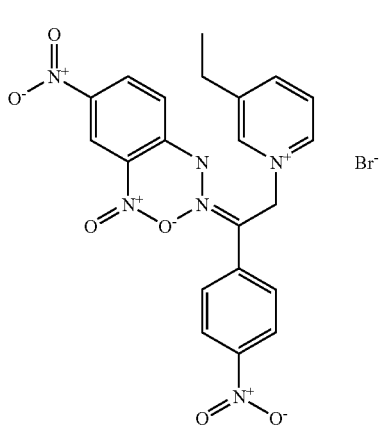
FORMULA XII-I
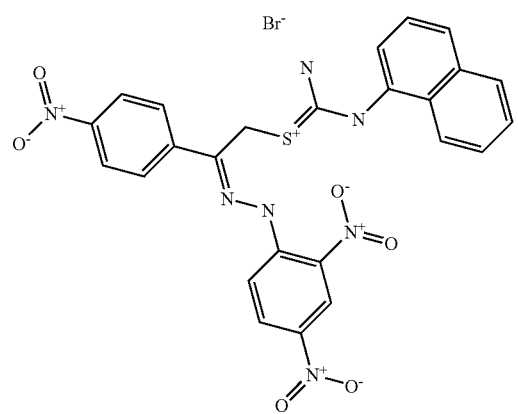
FORMULA XII-J
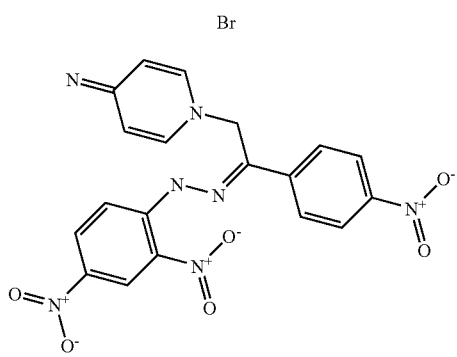

FORMULA XII-K
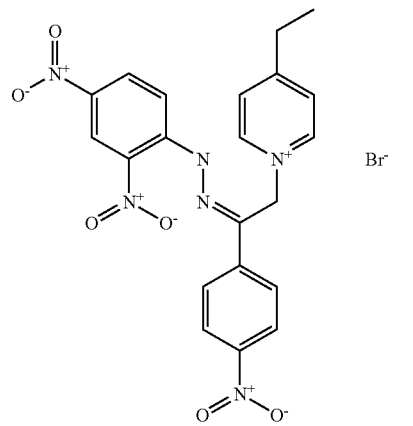
FORMULA XII-L
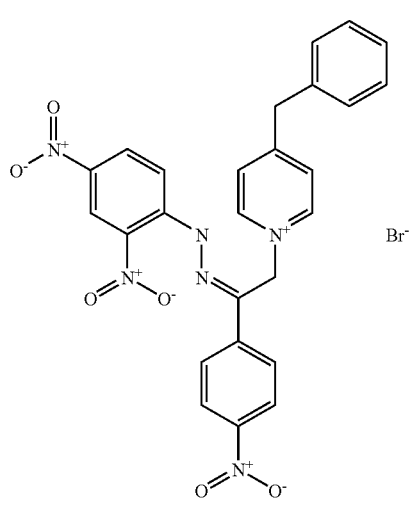
FORMULA XII-M
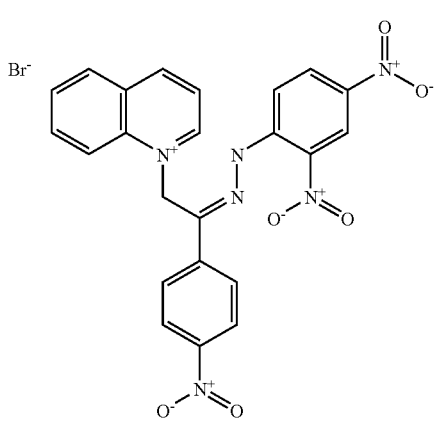
FORMULA XII-N
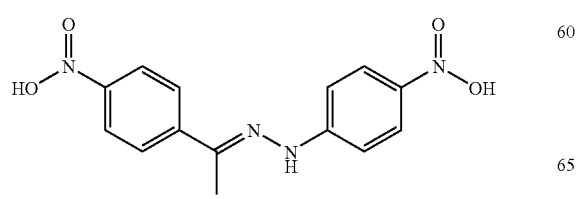
FORMULA XIII
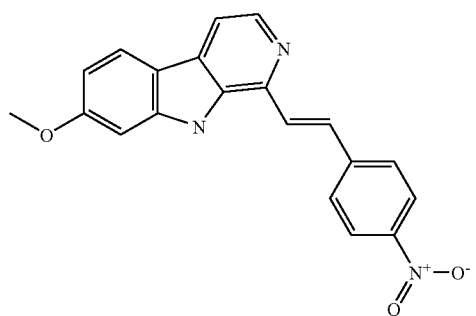
FORMULA XIV
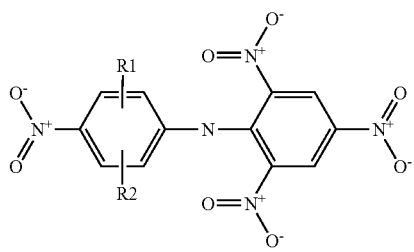
FORMULA XIV-A
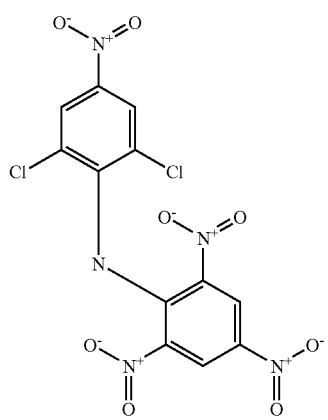
FORMULA XIV-B
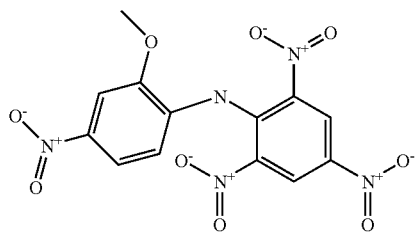
FORMULA XIV-C
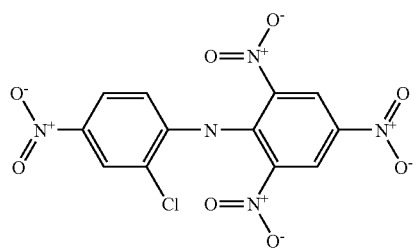

FORMULA XIV-D
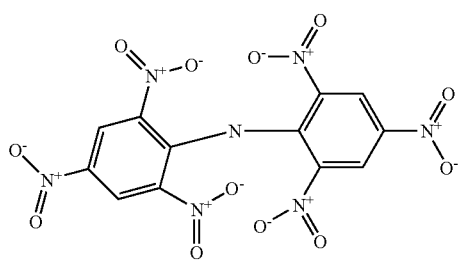
FORMULA XV
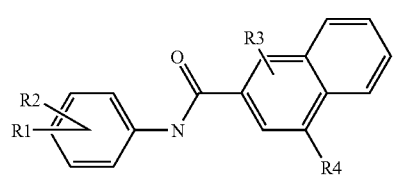
FORMULA 15-1-1
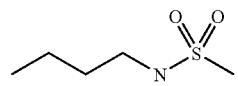
FORMULA 15-1-2
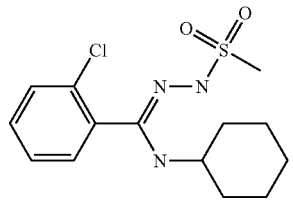
FORMULA 15-1-3
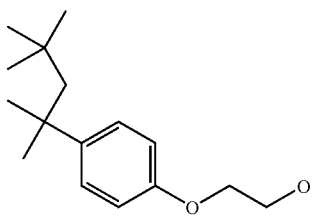
FORMULA 15-4-1
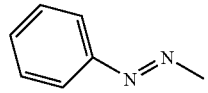
FORMULA 15-4-2
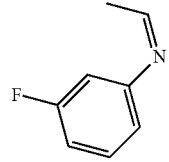
FORMULA 15-4-3
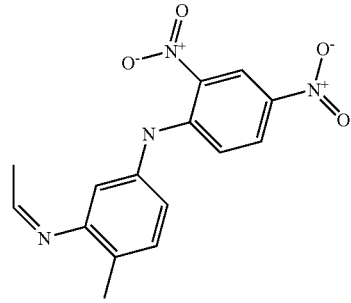
FORMULA 15-4-4
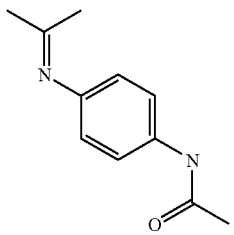
FORMULA 15-4-5
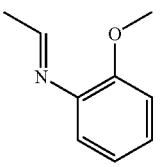
FORMULA 15-4-6
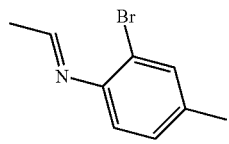
FORMULA 15-4-7
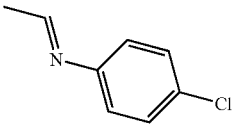
FORMULA 15-4-8
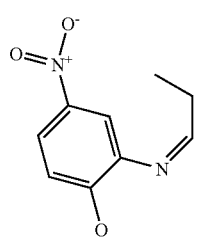
FORMULA 15-4-9
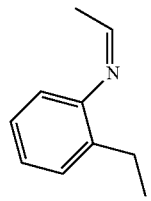
FORMULA 15-4-10
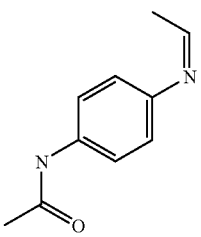
FORMULA 15-4-11
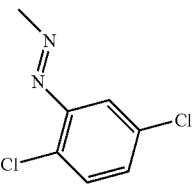

FORMULA 15-4-12
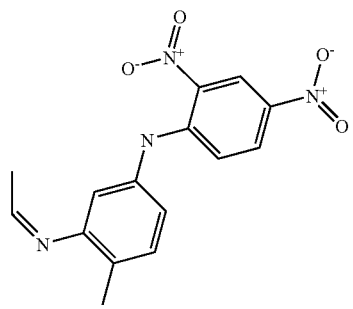
FORMULA XV-A
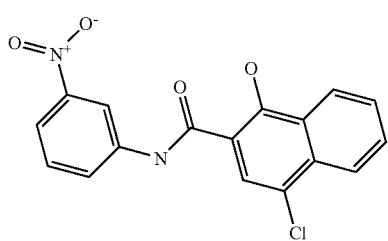
FORMULA XV-B
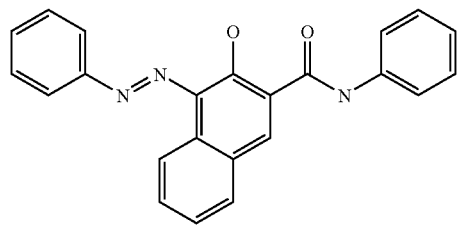
FORMULA XV-C
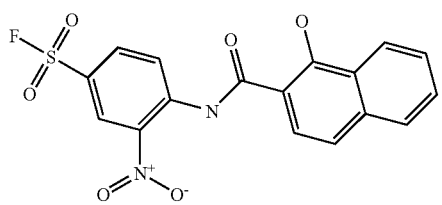
FORMULA XV-D
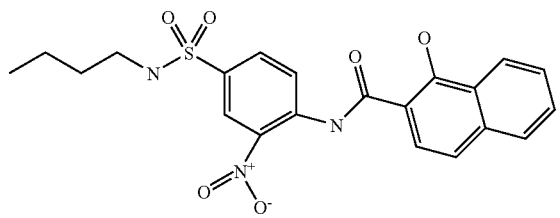
FORMULA XV-E
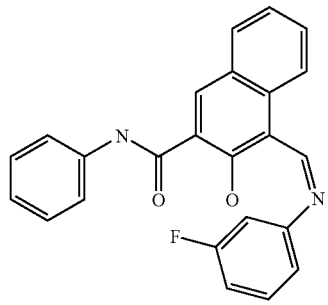
FORMULA XV-F
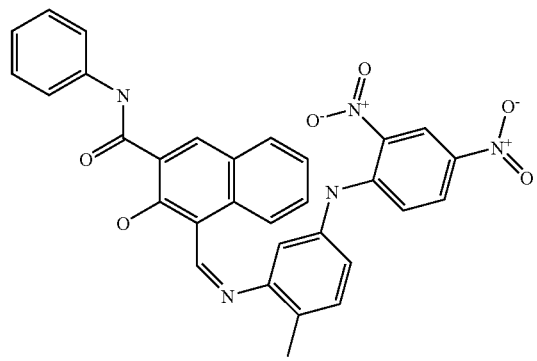
FORMULA XV-G
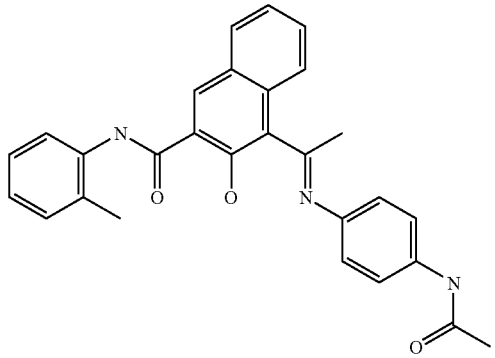
FORMULA XV-H
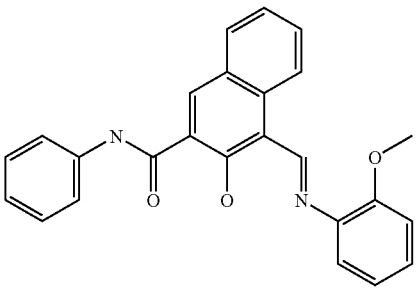
FORMULA XV-I
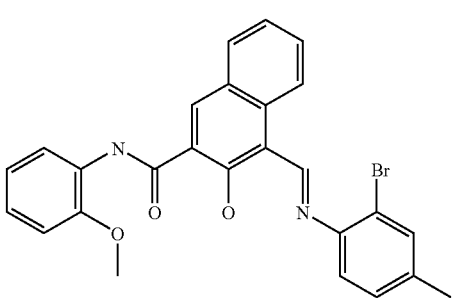

FORMULA XV-J
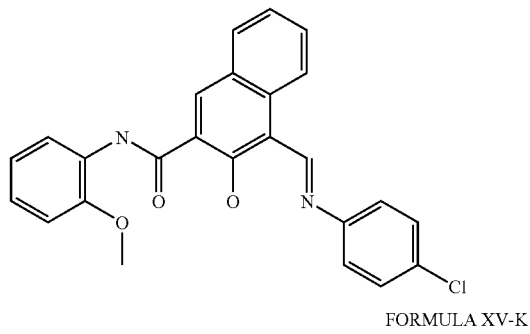
FORMULA XV-N
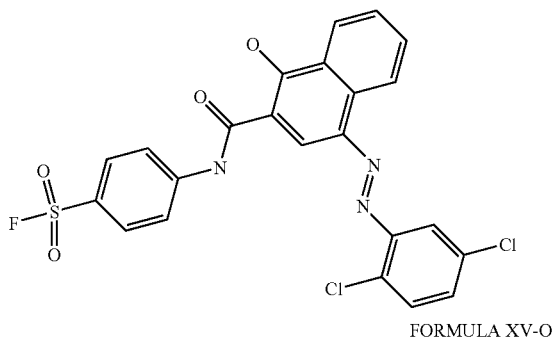
FORMULA XV-K
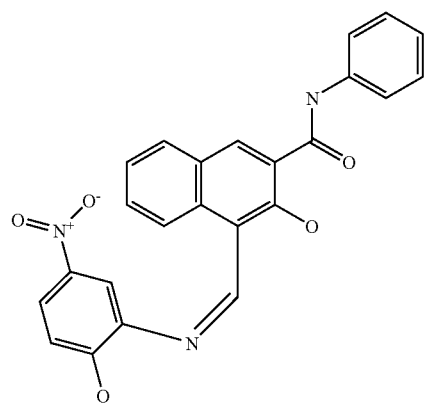
FORMULA XV-O
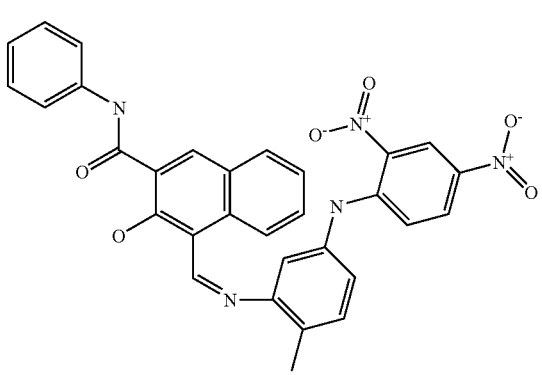
FORMULA XV-L
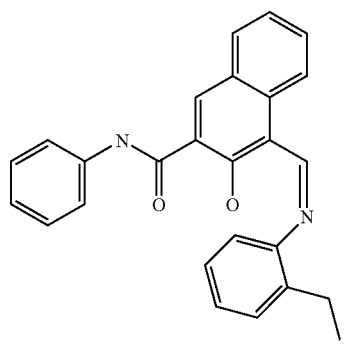
FORMULA XV-P
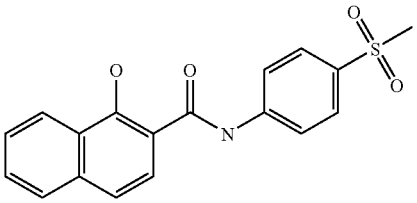
FORMULA XV-Q
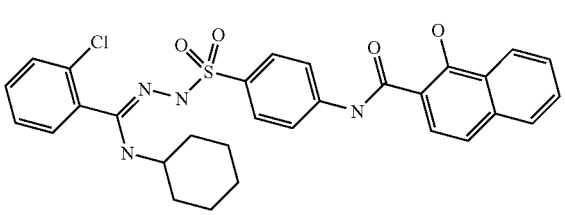
FORMULA XV-M
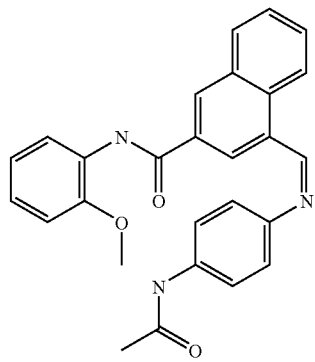
FORMULA XV-R
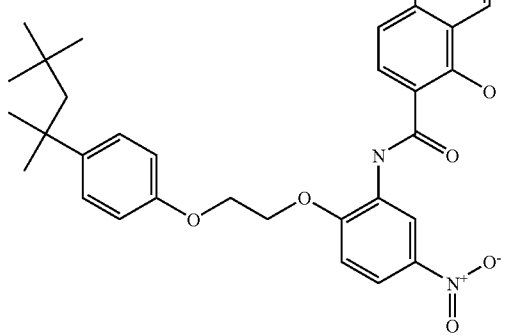

FORMULA XVI
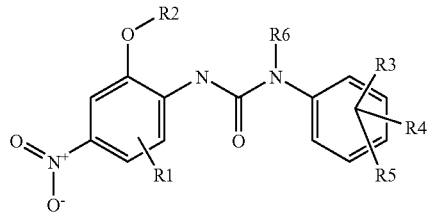
FORMULA 16-3-1
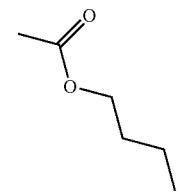
FORMULA XVI-A
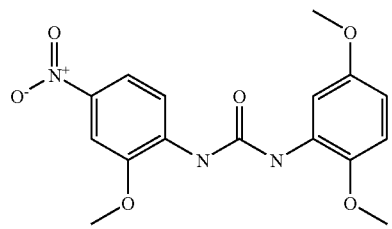
FORMULA XVI-B
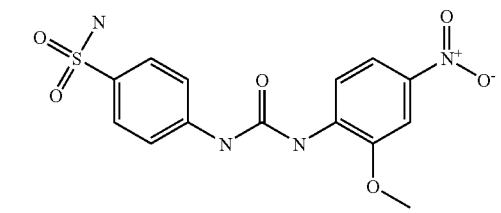
FORMULA XVI-C
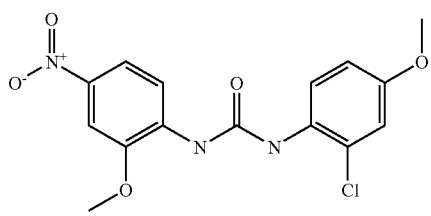
FORMULA XVI-D
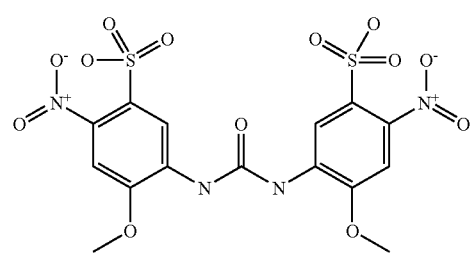
FORMULA XVI-E
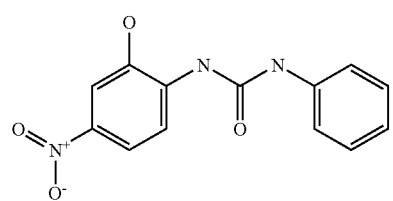
FORMULA XVI-F
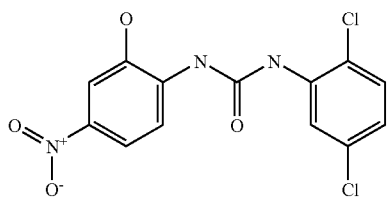
FORMULA XVI-G
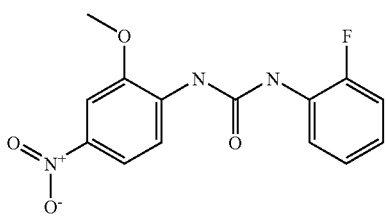
FORMULA XVI-H
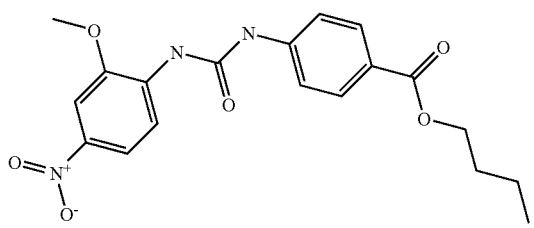
FORMULA XVI-I
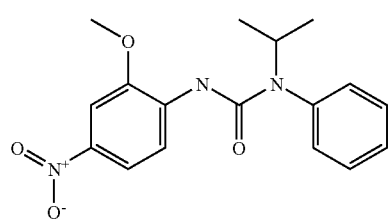
FORMULA XVI-J
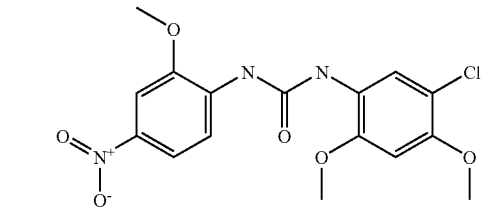
FORMULA XVI-K
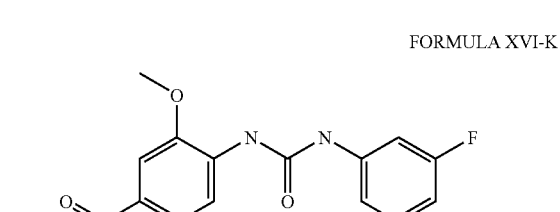

-continued

FORMULA XVI-L

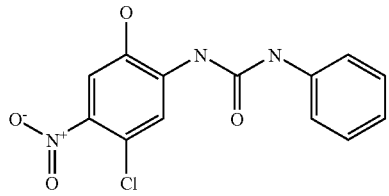

FORMULA XVI-M

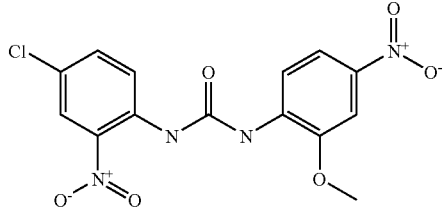

FORMULA XVI-N

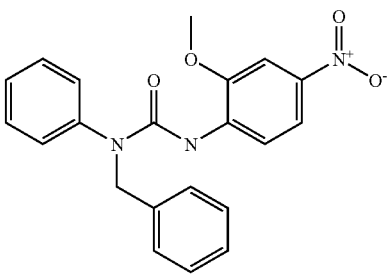

FORMULA XVII

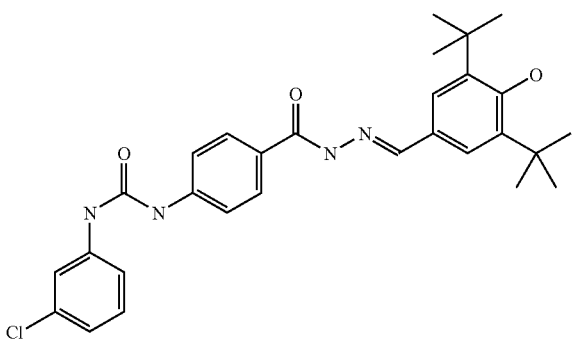

FORMULA XVIII

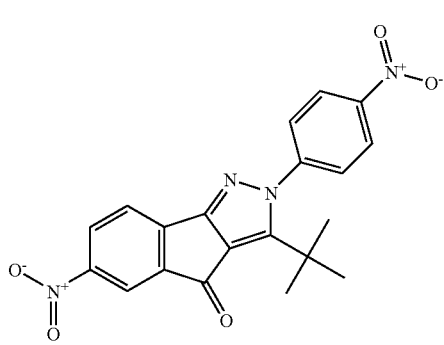

-continued

FORMULA XIX

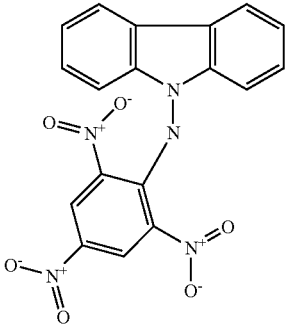

The invention claimed is:

1. A method of identifying a compound that is an allosteric modulator of an intermolecular interaction between a β-lactamase and a substrate at a functionally critical site of said β-lactamase which comprises:
   a) identifying an allosteric cavity on the β-lactamase that is within about 15 to 20 angstroms of said functionally critical site on the β-lactamase;
   b) calculating the dimensions of said cavity and mapping the chemical and/or electrostatic properties of said cavity;
   c) utilizing the calculated dimensions, chemical and/or electrostatic properties obtained in step b) to identify compounds that contain at least one functional group that can be accommodated by said cavity;
   d) testing said compounds in an in vitro assay to detect a compound which modulates the interaction at the functionally critical site between said β-lactamase and said substrate;
   thereby identifying said compound that is an allosteric modulator of said intermolecular interaction at said functionally critical site.

2. The method according to claim 1 wherein identifying the allosteric cavity within the structure of β-lactamase in step a) comprises using nuclear magnetic resonance, crystal structure analysis, calorimetric values from thermodynamic studies, or computer modeling.

3. The method according to claim 2, wherein the allosteric cavity is identified using nuclear magnetic resonance or crystal structure analysis, and further comprises identifying thermal β-factors.

4. The method according to any one of the preceding claims, wherein step c) comprises identifying compounds having at least one functional group that has shape complementarity to said cavity.

5. The method according to claim 4, wherein step d) comprises assaying said compounds in vitro to identify a compound that inhibits intermolecular interactions between β-lactamase and the substrate.

* * * * *